United States Patent
Sudoh et al.

(10) Patent No.: US 8,053,599 B2
(45) Date of Patent: *Nov. 8, 2011

(54) DRUG CONTAINING (2R)-2-PROPYLOCTANOIC ACID AS THE ACTIVE INGREDIENT

(75) Inventors: Masao Sudoh, Mishima-gun (JP); Seiichi Tanikawa, Mishima-gun (JP)

(73) Assignee: Ono Pharmaceutical Co., Ltd., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 10/574,477

(22) PCT Filed: Oct. 1, 2004

(86) PCT No.: PCT/JP2004/014892
§ 371 (c)(1), (2), (4) Date: Jan. 9, 2007

(87) PCT Pub. No.: WO2005/032536
PCT Pub. Date: Apr. 14, 2005

(65) Prior Publication Data
US 2007/0105956 A1    May 10, 2007

(30) Foreign Application Priority Data

Oct. 3, 2003    (JP) .................... 2003-345124

(51) Int. Cl.
*C07C 53/00* (2006.01)
(52) U.S. Cl. ............ 562/512; 562/401; 554/1; 554/124; 514/558
(58) Field of Classification Search .......... 562/401, 562/512; 554/1, 124; 514/558
See application file for complete search history.

(56) References Cited

U.S. PATENT DOCUMENTS

| | | | | |
|---|---|---|---|---|
| 6,043,223 | A * | 3/2000 | Black | 514/15 |
| 6,201,021 | B1 * | 3/2001 | Ohuchida et al. | 514/558 |
| 6,608,221 | B1 * | 8/2003 | Toda et al. | 554/1 |
| 2002/0022738 | A1 * | 2/2002 | Takada et al. | 560/142 |

FOREIGN PATENT DOCUMENTS

| | | |
|---|---|---|
| EP | 0987023 A1 | 3/2000 |
| EP | 1 153 910 A1 | 11/2001 |
| EP | 1 415 668 A1 | 5/2004 |
| EP | 1415668 A1 * | 5/2004 |
| EP | 1174131 B1 | 10/2006 |
| JP | 7-82146 A | 3/1995 |
| JP | 7-285911 A | 10/1995 |
| JP | 07285911 A * | 10/1995 |
| JP | 8-53351 A | 2/1996 |
| JP | 8-291106 A | 11/1996 |
| JP | 8-295648 A | 11/1996 |
| JP | 8291106 * | 11/1996 |
| JP | 2002-97158 A | 4/2002 |
| WO | WO 00/48982 A1 | 8/2000 |
| WO | WO 03/007992 A1 | 1/2003 |

OTHER PUBLICATIONS

T.Hasegawa, H.Yamamoto A practical synthesis of optically active (R)-2-propyloctanoic acid: Therapeutic agent for Alzheimer's disease Bull.Chem.Soc. Jpn. 2000, 73, 423-428.*
T. Hasegawa and H.Yamamoto, Bull.Chem.Soc.Jpn., 73, 423-428, 2000.*
"Shin Yakuzaigaku Soron", Apr. 10, 1987, pp. 322-331.
Indian First Examination Report dated Sep. 30, 2008.
European Office Action dated Mar. 12, 2010 in European application No. 04792177.0.
Notification of Defects in Patent Application No. 174655 issued by the Israeli Patent Office, dated Sep. 6, 2010.
Japanese Office Action issued on Oct. 1, 2010 in the corresponding Japanese Patent Application No. 2005-514507.

* cited by examiner

*Primary Examiner* — Sudhakar Katakam
(74) *Attorney, Agent, or Firm* — Sughrue Mion, PLLC

(57) ABSTRACT

The present invention relates to a medicament which is useful for neurodegenerative diseases, which comprises about 1 to about 5 equivalents of a basic metal ion based on 1 equivalent of (2R)-2-propyloctanoic acid or a salt thereof, which is supplied from a metal salt of weak acid or a metal hydroxide, and optionally further comprises an additive. The medicament of the present invention is a medicament which a pH of suitable for intravenous administration, is resistant to fluctuations of the pH and is not clouded when it is dissolved in an infusion, and an injection and the like can be prepared therefrom by using any dissolving liquid and/or dilution liquid.

17 Claims, 3 Drawing Sheets

Confirmation of micelle formation

DRUG CONTAINING (2R)-2-PROPYLOCTANOIC ACID AS THE ACTIVE INGREDIENT

TECHNICAL FIELD

The present invention relates to a medicament comprising (2R)-2-propyloctanoic acid or a salt thereof in a high concentration, which is useful as an agent for treating neurodegenerative diseases including cerebral infarction, and a process for producing the same.

BACKGROUND ART

Patients with cerebral stroke in general are often taken to hospitals only after they fall unconscious due to cerebral infarction or cerebral hemorrhage, and such a patient with cerebral stroke receives treatment unavoidably while remaining unconscious. Therefore, a medicament administered for the treatment of such a disease is preferably a preparation suitable for parenteral administration such as an injection. Particularly, in an expectation of rapid expression of the effect, it is preferably an injection for intravenous administration. At present, Radicut (edaravone) and t-PA, which are used as agents for treating cerebral infarction, are all injections for intravenous administration.

Meanwhile, it is well known that the most important factor for a medicament is stability, since such a product is necessarily subjected to a long-term stability test lasting for several months in the development stage. Generally, a chemical substance is more stable in the solid state rather than the liquid state and as a solution in a high concentration rather than that in a low concentration. Thus, even for certain medicaments that should be administered to patients as dilute solutions, many of them are supplied in a more stable form, which can be administered to a patient only after being subjected to the operation of dissolution or dilution at the time of use by means of direct manipulation of a person involved in medical services such as a doctor or a nurse. An injection, in particular, can be stored for longer periods of time and can have more stable quality when it is supplied in the form of a liquid in a high concentration such as an enriched injection or a concentrated injection, or in the solid form such as a lyophilized preparation.

Meanwhile, as examples of an injection comprising (2R)-2-propyloctanoic acid or a salt thereof, which is useful as an agent for treating or preventing various cerebral nerve diseases including cerebral stroke, the injections described in the following have been reported.

A pentanoic acid derivative which is useful as an agent for cerebral function improvement is known to be used as an injection, upon mixing with at least one inert aqueous diluting agent (distilled water for injection, saline, etc.) or at least one inert non-aqueous diluting agent (propylene glycol, polyethylene glycol, etc.) (see, for example, the specifications of EP 0632008 and EP 1174131). These publications describe that an injection can further comprise auxiliaries such as a preservative, a wetting agent, an emulsifier, a dispersing agent, a stabilizing agent and a solubilizing aid.

However, there is not available any known literature that specifically discloses an injection comprising (2R)-2-propyloctanoic acid or a salt thereof, or any report on a medicament comprising (2R)-2-propyloctanoic acid or a salt thereof in a high concentration for the formulation of an injection.

DISCLOSURE OF THE INVENTION

The present inventors have attempted to prepare a medicament comprising (2R)-2-propyloctanoic acid or a salt thereof in a high concentration, which is useful for the treatment of neurodegenerative diseases including cerebral infarction, and which can be formulated to an injection which can be conveniently administered to a patient, if necessary, by means of the dissolution or dilution operation. However, they have found that when an injection comprising the substance is prepared, there are critical problems such as that the product cannot be intravenously administered because (1) since (2R)-2-propyloctanoic acid is an oil, it is insoluble and immiscible in water; and (2) since a salt, for example, a sodium salt, of (2R)-2-propyloctanoic acid is in a wax form, it is difficult to handle when using the substance as a drug substance for a medicament, and moreover, even if dissolved in water, the substance has a high pH and is susceptible to clouding under slight fluctuations of the pH. The inventors have conducted studies to solve these problems and have found as a result that (2R)-2-propyloctanoic acid can be dissolved in water in a high concentration by mixing it with a strong alkali such as sodium hydroxide. However, it was found that a highly concentrated solution of (2R)-2-propyloctanoic acid as prepared by dissolving in the above-described manner has a high pH, and is clouded when diluted in order to formulate an injection appropriate for administration to a patient, using an aqueous diluting liquid, e.g., saline, depending on the dilution concentration; or even when the solution is initially in the dissolved state, it is clouded, resulting from slight fluctuation of pH, particularly by a shift to the acidic side, in a way similar to the case of the sodium salt described above. Moreover, the solution in a high concentration was difficult to be stored for a long period of time because of the appearance of insoluble allotrio within the solution under long-term storage in conventional glass containers. Thus, there are problems in using a drug which is sensitive to a change in the drug concentration or in the pH of the solution, leading to a change such as clouding. That is, there is in fact the risk of clouding of the drug, upon preparing an injection which can be administered to a patient, by direct manipulation of a person involved in medical services, for combined use with other agents, or during the action of intravascular administration to a patient. Furthermore, an agent which generates insoluble allotrio during storage cannot be provided for an application as a medicament.

Therefore, a purpose of the present invention is to provide a medicament comprising (2R)-2-propyloctanoic acid or a salt thereof in a high concentration, which is resistant to fluctuations of the pH and can be formulated to an injection having a pH suitable for administration to a patient, without clouding, by using a dissolving liquid and/or a diluting liquid at the time of use; and a process for producing the same.

Moreover, another purpose of the present invention is to provide a medicament comprising (2R)-2-propyloctanoic acid or a salt thereof in a high concentration, which does not exhibit the problems of generating insoluble allotrio even under long-term storage.

The inventors continued intensive studies and eventually found for the first time that it is possible to provide a medicament comprising (2R)-2-propyloctanoic acid or a salt thereof in a high concentration, which is useful as a therapeutic and/or prophylactic agent for various neurodegenerative diseases including cerebral infarction, and free from the above-described problems, by addition of a certain amount of a basic metal ion. The inventors conducted a detailed research based on this finding to accomplish the present invention.

Thus, the present invention relates to the followings and the like:

(1) A medicament comprising (2R)-2-propyloctanoic acid or a salt thereof and a basic metal ion.

(2) The medicament according to the above (1), which is a liquid.
(3) The medicament according to the above (1), which is a semi-solid.
(4) The medicament according to the above (1), which comprises about 1 to about 5 equivalents of the basic metal ion based on 1 equivalent of (2R)-2-propyloctanoic acid or a salt thereof.
(5) The medicament according to the above (2), which is a micelle water dispersion liquid.
(6) The medicament according to the above (1), which comprises at least one selected from a metal salt of phosphoric acid, a metal salt of carbonic acid and a metal salt of sulfurous acid, and optionally further comprises a metal hydroxide, as a source(s) of the basic metal ion.
(7) The medicament according to the above (1), which comprises at least one selected from trisodium phosphate, disodium hydrogen phosphate, sodium dihydrogen phosphate, sodium carbonate, sodium hydrogen carbonate, sodium sulfite, sodium hydrogen sulfite, tripotassium phosphate, dipotassium hydrogen phosphate, potassium dihydrogen phosphate, potassium carbonate, potassium hydrogen carbonate, potassium sulfite and potassium hydrogen sulfite, and optionally further comprises sodium hydroxide and/or potassium hydroxide, as a source(s) of the basic metal ion.
(8) The medicament according to the above (7), wherein the source of the basic metal ion is (i) trisodium phosphate, (ii) disodium hydrogen phosphate and sodium hydroxide, or (iii) sodium dihydrogen phosphate and sodium hydroxide.
(9) The medicament according to the above (2), which has a pH of about 7.0 to about 12.0.
(10) The medicament according to the above (9), wherein the pH is about 8.4 to about 9.0.
(11) The medicament according to the above (1), which comprises about 1 to about 5 equivalents of the basic sodium ion based on 1 equivalent of (2R)-2-propyloctanoic acid or a salt thereof; comprises at least one selected from a sodium salt of phosphoric acid and a sodium salt of carbonic acid, and optionally further comprises sodium hydroxide, as a source(s) of the basic sodium ion; and has a pH of about 8.4 to about 9.0.
(12) The medicament according to the above (1), wherein the salt of (2R)-2-propyloctanoic acid is a sodium salt or a basic natural amino acid salt.
(13) The medicament according to the above (2), which comprises about 2.5 to about 100 mg of (2R)-2-propyloctanoic acid or a salt thereof per mL.
(14) The medicament according to the above (1), which is filled in a plastic container, a glass container of which inner surface is coated with silicone, or a glass container of which inner surface is surface-treated with silicon dioxide.
(15) The medicament according to the above (1), which is obtainable by dissolving (2R)-2-propyloctanoic acid in an aqueous solution comprising about 1 to about 5 equivalents of the basic metal ion based on 1 equivalent of (2R)-2-propyloctanoic acid.
(16) A medicament having improved solubility in an infusion, which is prepared by using (2R)-2-propyloctanoic acid and about 1 to about 5 equivalents of a basic metal ion based on 1 equivalent of (2R)-2-propyloctanoic acid.
(17) The medicament according to the above (1), which is an agent for preventing and/or treating neurodegenerative diseases, nerve disorders or diseases in need of nerve regeneration.
(18) A process for producing a medicament comprising (2R)-2-propyloctanoic acid or a salt thereof and a basic metal ion, which comprises dissolving (2R)-2-propyloctanoic acid or a salt thereof, one or at least two selected from a metal salt of phosphoric acid, a metal salt of carbonic acid and a metal salt of sulfurous acid, and optionally metal hydroxide in water to thereby prepare a solution comprising about 2.5 to about 100 mg/mL of (2R)-2-propyloctanoic acid or a salt thereof and having a pH of about 8.4 to about 9.0; and filling the solution into a plastic container or a glass container of which inner surface is surface-treated with silicon dioxide, followed by high pressure steam sterilization.
(19) A method for using a basic metal ion, which comprises preparing about 1 to about 5 equivalents of the source of the basic metal ion based on 1 equivalent of (2R)-2-propyloctanoic acid and water as a solvent; and mixing (2R)-2-propyloctanoic acid with water in the presence of the basic metal ion to thereby dissolve (2R)-2-propyloctanoic acid in water.
(20) A metal salt or a basic natural amino acid salt of (2R)-2-propyloctanoic acid.
(21) The salt according to the above (20), which is a monovalent alkali metal salt.
(22) The salt according to the above (21), which is (2R)-2-propyloctanoic acid-sodium salt.
(23) A medicament comprising (2R)-2-propyloctanoic acid or a salt thereof, which is a liquid having a pH of about 7.0 to about 12.0.
(24) The medicament according to the above (23), wherein the pH is about 8.4 to about 9.0.
(25) The medicament according to the above (23), which is aqueous.
(26) The medicament according to the above (23), which further comprises a basic metal ion.
(27) The medicament according to the above (26), wherein the source of the basic metal ion is disodium hydrogen phosphate and sodium hydroxide.
(28) The medicament according to the above (27), which comprises, per mL, about 50 mg of (2R)-2-propyloctanoic acid, about 80 mg of disodium hydrogen phosphate-dodecahydrate and sodium hydroxide; and has a pH of about 8.4 to about 9.0.
(29) A container made of plastics, which is filled with 4 mL, 8 mL or 20 mL of the medicament according to the above (28).
(30) The container according to the above (29), which is an ampoule made of polyethylene or polypropylene, or a syringe made of cyclic polyolefin.
(31) A method for preventing and/or treating neurodegenerative diseases, nerve disorders or diseases in need of nerve regeneration, which comprises administering an effective amount of the medicament according to the above (1) to a mammal.
(32) Use of the medicament according to the above (1) for the manufacture of an agent for preventing and/or treating neurodegenerative diseases, nerve disorders or diseases in need of nerve regeneration.
(33) A medicament comprising (2R)-2-propyloctanoic acid and about 1 to about 5 equivalents of a basic sodium ion based on 1 equivalent of (2R)-2-propyloctanoic acid, which comprises disodium hydrogen phosphate and sodium hydroxide as sources of the basic sodium ion; and has a pH of about 8.4 to about 9.0.
(34) The medicament according to the above (33), which is filled in an ampoule made of polyethylene or polypropylene, or in a syringe made of cyclic polyolefin.

(2R)-2-Propyloctanoic acid used in the present invention is a compound represented by formula (I):

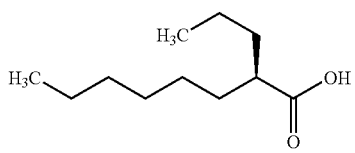

wherein ▰ represents β-configuration.

The salt of (2R)-2-propyloctanoic acid is preferably a pharmaceutically acceptable salt. The pharmaceutically acceptable salt is preferably a non-toxic water-soluble salt.

Examples of suitable salt of (2R)-2-propyloctanoic acid, for example, include salts with inorganic bases, salts with organic bases, salts with basic natural amino acids and the like.

The salt with an inorganic base is preferably, for example, an alkali metal salt (for example, a sodium salt, a potassium salt, a lithium salt, etc.), an ammonium salt (for example, a tetramethylammonium salt, a tetrabutylammonium salt, etc.), or the like.

The salt with an organic base is preferably, for example, a salt with alkylamine (for example, methylamine, dimethylamine, trimethylamine, triethylamine, etc.), heterocyclic amine (for example, pyridine, picoline, piperidine, etc.), alkanolamine (for example, ethanolamine, diethanolamine, triethanolamine, etc.), dicyclohexylamine, N,N'-dibenzylethylenediamine, cyclopentylamine, benzylamine, phenethylamine, tris(hydroxymethyl)methylamine, N-methyl-D-glucamine or the like.

The salt with a basic natural amino acid is not particularly limited, so long as it is a salt with a basic amino acid which is naturally present and can be purified, and it is preferably, for example, a salt with arginine, lysine, ornithine, histidine or the like. Among these, more preferred are, for example, an alkali metal salt or a basic natural amino acid salt, and particularly preferred is a sodium salt.

In the present invention, (2R)-2-propyloctanoic acid or a salt thereof is not limited to those which are substantially pure single substances, and they may include impurities (for example, byproducts, solvents, starting materials, etc. which originate from the preparation process, or decomposition products, etc.) within the scope acceptable in an active ingredient for a medicament. The contents of the impurities acceptable in an active ingredient for a medicament may depend on the impurities contained, but the contents are preferably, for example, about 20 ppm or less for heavy metals, about 1.49% by weight or less for the (S)-isomer which is an optical isomer, about 5,000 ppm or less in total for residual solvents such as 2-propanol or heptane, and about 0.2% by weight or less for water, respectively.

(2R)-2-Propyloctanoic acid or a salt thereof can be prepared by methods known per se, for example, the methods described in the specification of EP 0632008, the specification of WO 99/58513, the specification of WO 00/48982, the specification of JP 3032447 (registration number), the specification of JP 3084345 (registration number) and the like, or by appropriate combinations of such methods.

For example, an alkali metal salt or a basic natural amino acid salt of (2R)-2-propyloctanoic acid can be prepared by mixing, in an alcohol-based solvent (for example, methanol, ethanol, etc.) or an ether-based solvent (for example, dioxane, etc.), (2R)-2-propyloctanoic acid with 1 equivalent of an alkali metal hydroxide (for example, sodium hydroxide, potassium hydroxide, etc.) or with 1 equivalent of a basic natural amino acid (for example, arginine, lysine, etc.) in the presence or absence of water, and reacting the mixture at 0 to 40° C.

The reaction product may be purified by conventional purification means, for example, by distillation at atmospheric or reduced pressure, high performance liquid chromatography using silica gel or magnesium silicate, thin layer chromatography or column chromatography, or by conventional methods such as washing and recrystallization. Also, if necessary, the product may be subjected to treatments such as lyophilization.

The solubility in water of (2R)-2-propyloctanoic acid can be improved by converting the compound to its salt.

The medicament of the present invention means an injection precursor which can be formulated to an injection that can be administered to a patient, by using a dissolving liquid and/or a diluting liquid or the like at the time of use.

The medicament of the present invention is not limited in its form. That is, the medicament of the present invention may be a liquid medicament which is generally referred to as an enriched injection or a concentrated injection, or a solid medicament such as a lyophilized medicament. Furthermore, it may be a semi-solid medicament in the form of gel.

In the case of a liquid medicament, an injection can be formulated by directly using a diluting liquid; and in the case of a solid or semi-solid medicament, an injection can be formulated by first providing a solution having a high concentration by using a dissolving liquid and then diluting the solution with a diluting liquid. Although it is possible to use a solid or semi-solid medicament directly as an injection, in this case it may be difficult to provide homogeneous dissolution or dispersion.

Thus, the medicament of the present invention is preferably a liquid, and particularly preferred is an aqueous medicament, that is, a medicament in which a medium is substantially water. Especially, an aqueous medicament having a pH of about 7.0 or more (for example, preferably in the range from about 7.0 to about 12.0, and more preferably in the range from about 8.4 to about 9.0) is preferred. Furthermore, in the case of a solid medicament or a semi-solid medicament, a medicament having a pH of about 7.0 or more (for example, preferably in the range from about 7.0 to about 12.0, and more preferably in the range of about 8.4 to about 9.0) when formulated into a liquid in a high concentration using a dissolving liquid, is preferred.

In the specification of the present invention, an injection may be a liquid injectable composition which can be directly administered parenterally to a patient, and thus the injection prepared by using the medicament of the present invention may be in the form of, for example, an aqueous injection, a non-aqueous injection, a suspension injection, an emulsion injection, an infusion or the like. Furthermore, the prepared injection can be applied to tissues intramuscularly, intradermally, subcutaneously, intravenously, intraarterially, intraperitoneally, intrathecally or the like.

The medicament of the present invention comprises a basic metal ion, in addition to the active ingredient (2R)-2-propyloctanoic acid or a salt thereof.

In the specification of the present invention, the term "basic metal ion" means a metal ion supplied by a metal compound in an aqueous solution, and preferably a metal ion supplied by a metal compound showing alkalinity in an aqueous solution. The basic metal ion is present as a metal ion when the medicament of the present invention is a liquid, and as a potential metal ion when the medicament of the present invention is a solid or a semi-solid.

The term "potential metal ion" as used herein means the metal in a metal compound which becomes a metal ion when the metal compound is brought to the state capable of ionization (for example, an aqueous solution, etc.), for example, by means of operation such as addition of water.

The metal compound which serves as the source of the basic metal ion is not particularly limited, and includes, for example, a metal salt of weak acid, metal hydroxide and the like.

The weak acid which constitutes a metal salt of weak acid may be organic or inorganic acid, or even polyvalent acid. The weak acid includes, for example, phosphoric acid, carbonic acid, boric acid, sulfurous acid, organic sulfonic acid, C2-6 organic carboxylic acids (for example, mono- to trivalent C2-6 organic carboxylic acids, i.e., C2-6 aliphatic monocarboxylic acids, dicarboxylic acids or tricarboxylic acids, etc.), and other organic acids. The metal salt of weak acid of the present invention includes, for example, the salts formed by those weak acids with monovalent alkali metals (for example, sodium, potassium, lithium, rubidium, cesium, francium, etc.).

As the monovalent alkali metal, for example, sodium, potassium, lithium and the like are preferred, with sodium and potassium being more preferred. Particularly preferred is sodium.

The metal salt of weak acid according to the present invention includes, for example, metal salts of phosphoric acid: preferably disodium hydrogen phosphate, sodium dihydrogen phosphate, trisodium phosphate, dipotassium hydrogen phosphate, potassium dihydrogen phosphate, tripotassium phosphate and the like; metal salts of carbonic acid: preferably sodium carbonate, sodium hydrogen carbonate, potassium carbonate, potassium hydrogen carbonate and the like; metal salts of boric acid: preferably sodium borate, potassium borate and the like; metal salts of sulfurous acid: preferably sodium sulfite, sodium hydrogen sulfite, potassium sulfite, potassium hydrogen sulfite and the like; metal salts of organic sulfonic acid: preferably sodium camphorsulfonate, sodium methanesulfonate, sodium ethanesulfonate, sodium trifluoromethanesulfonate, sodium toluenesulfonate, sodium naphthalenesulfonate, sodium 2-hydroxyethanesulfonate, sodium aminoethanesulfonate, potassium camphorsulfonate, potassium methanesulfonate, potassium ethanesulfonate, potassium trifluoromethanesulfonate, potassium toluenesulfonate, potassium naphthalenesulfonate, potassium 2-hydroxyethanesulfonate, potassium aminoethanesulfonate and the like; and metal salts of C2-6 organic carboxylic acids: preferably sodium acetate, sodium propionate, sodium valerate, sodium oxalate, sodium ascorbate, sodium lactate, sodium succinate, sodium citrate, disodium citrate, sodium malate, sodium tartrate, sodium maleate, sodium fumarate, sodium aminoacetate, potassium acetate, potassium propionate, potassium valerate, potassium oxalate, potassium ascorbate, potassium lactate, potassium succinate, potassium citrate, disodium citrate, potassium malate, potassium tartrate, potassium maleate, potassium fumarate, potassium aminoacetate and the like.

In addition to these, use can be also made of, for example, sodium aspartate, sodium glutamate, sodium acetyltryptophan, sodium caprylate, sodium gluconate, sodium salitylate, sodium diethylenetriamine pentaacetate, sodium thioglycolate, potassium thiocyanate, sodium thiosulfate, sodium deoxycholate, potassium pyrosulfite, sodium pyrosulfite, sodium methanesulfobenzoate, sodium benzoate, sodium pyrophosphate, potassium aspartate, potassium glutamate, potassium acetyltryptophan, potassium caprylate, potassium gluconate, potassium salitylate, potassium diethylenetriamine pentaacetate, potassium thioglycolate, sodium thiocyanate, potassium thiosulfate, potassium deoxycholate, potassium methanesulfobenzoate, potassium benzoate, potassium pyrophosphate and the like.

The metal salt of weak acid according to the present invention preferably includes, for example, a metal salt of phosphoric acid, a metal salt of carbonic acid, a metal salt of sulfurous acid or the like. In particular, metal salts of phosphoric acid (for example, trisodium phosphate, disodium hydrogen phosphate, sodium dihydrogen phosphate, tripotassium phosphate, dipotassium hydrogen phosphate, potassium dihydrogen phosphate, etc.) are preferred, with trisodium phosphate or disodium hydrogen phosphate being particularly preferred.

Such a metal salt of weak acid can be incorporated into the medicament of the present invention, not only in their anhydrous form but also in the form of solvate such as hydrate (for example, in the case of metal phosphate, in particular sodium phosphate, trisodium phosphate-dodecahydrate, sodium dihydrogen phosphate-dihydrate, disodium hydrogen phosphate-dodecahydrate, etc.).

The metal salt of weak acid is mixed in the solution state or in the solid sate.

Furthermore, the metal salts of weak acids may be used in combination of two or more components, if necessary.

Among the metal salts of weak acids, preferred is a metal salt having its pKa value in the basic pH range. In the case of metal salts of polyvalent weak acids, preferred is a metal salt having at least one of its plural pKa values in the basic pH range.

In the specification of the present invention, the metal hydroxide includes, for example, the hydroxides of the monovalent alkali metals described above. Specific examples include sodium hydroxide, potassium hydroxide, lithium hydroxide, rubidium hydroxide, cesium hydroxide, francium hydroxide and the like, and among these, preferred are, for example, sodium hydroxide, potassium hydroxide, lithium hydroxide and the like, with sodium hydroxide or potassium hydroxide being more preferred. Particularly preferred is sodium hydroxide.

Such metal hydroxide is mixed in the solution state or in the solid state.

Furthermore, the metal hydroxide may be used in combination of two or more compounds, if necessary.

In the medicament of the present invention, the metal salt of weak acid added as the source of the basic metal ion also functions as a buffering agent and as a dissolving agent. It is possible to prepare the medicament of the present invention which is resistant to fluctuations of the pH, by means of the metal salt of weak acid since it is dissociated in the medicament, more specifically in the injection, and interacts with metal hydroxide, or (2R)-2-propyloctanoic acid or a salt thereof.

Specifically, for example, in an aqueous medicament comprising (2R)-2-propyloctanoic acid and trisodium phosphate, the (2R)-2-propyloctanoic acid is converted to (2R)-2-propyloctanoic acid sodium salt by means of sodium ions donated by trisodium phosphate and is dissolved in water. Furthermore, trisodium phosphate is converted, as it releases sodium ions in the aqueous solution, to disodium hydrogen phosphate and further to sodium dihydrogen phosphate. When such substances co-exist in equilibrium in the aqueous medicament, that is, the aqueous solution, the medicament of the present invention attains the buffering ability.

In another embodiment, for example, in an aqueous medicament comprising (2R)-2-propyloctanoic acid and disodium hydrogen phosphate as well as sodium hydroxide, the (2R)-

2-propyloctanoic acid is converted to (2R)-2-propyloctanoic acid-sodium salt by means of sodium ions donated by sodium hydroxide and/or disodium hydrogen phosphate, and is dissolved in water. Sodium hydroxide and/or disodium hydrogen phosphate, as they exchange sodium ions in the aqueous solution, are placed in the state where trisodium phosphate is added, that is, the state wherein disodium hydrogen phosphate and sodium dihydrogen phosphate co-exist in the aqueous solution, or in a state approximating the former state, and come to exist in equilibrium, and thus to exhibit the buffering ability.

Thus, with regard to the medicament of the present invention, the metal salt of weak acid interacts with metal hydroxide, or (2R)-2-propyloctanoic acid or a salt thereof and exhibits the same effect as in the case of adding a monobasic phosphate-dibasic phosphate based buffer, or a carbonate-hydrogen carbonate based buffer, so that the medicament of the present invention can attain the buffering ability.

In the medicament of the present invention, metal hydroxide which is added as the source of a basic metal ion also functions as a dissolving agent or a pH adjusting agent. That is, the metal hydroxide may be used for adjusting the pH or for dissolving (2R)-2-propyloctanoic acid or a salt thereof.

As described above, the medicament of the present invention may be a liquid, a solid or a semi-solid, and when the inventive medicament is a liquid medicament, particularly an aqueous medicament, for example, the metal hydroxide can be used to dissolve (2R)-2-propyloctanoic acid or a salt thereof at a high concentration.

Furthermore, when the inventive medicament is a solid or semi-solid medicament, upon preparation of a liquid in a high concentration using any dissolving liquid (preferably, water (e.g., water for injection, etc.), or the like), the metal hydroxide may be added to dissolve (2R)-2-propyloctanoic acid or a salt thereof.

Addition of metal hydroxide would be necessary for the medicament of the present invention, for example, when the above-described metal salt of weak acid is insufficient, or when the pH of the medicament in a preferred range (pH 7.0 or more, more preferably pH 7.0 to 12.0, and particularly preferably pH 8.4 to 9.0) may not be achieved with the metal salts of weak acids only, or when (2R)-2-propyloctanoic acid or a salt thereof does not dissolve, or the like. Under such circumstances, the amount of the metal salt of weak acid may be increased to a desired range, or (2R)-2-propyloctanoic acid or a salt thereof may be dissolved by addition of metal hydroxide.

In the medicament of the present invention, the content of the above-described metal compound (metal salt of weak acids, metal hydroxide or the like) is not particularly limited, but it will be preferable that the content of the basic metal ion supplied by the metal compound is in the range of about 1 to about 5 equivalents, and more preferably about 1.2 to about 3.5 equivalents based on 1 equivalent of (2R)-2-propyloctanoic acid or a salt thereof.

In the medicament of the present invention, the metal compounds, that is, the metal salts of weak acids or metal hydroxides, may be used alone or in combination as the source of the basic metal ion, and it is preferable to use at least one metal salt of weak acid.

When only metal hydroxide is used as the source of the basic metal ion, for example, when about 1 equivalent (for example, 0.95 equivalent or the like) of sodium hydroxide is used based on 1 equivalent of (2R)-2-propyloctanoic acid, it is possible to dissolve (2R)-2-propyloctanoic acid in water (for example, water for injection or the like); however, the resulting solution has a high pH, and occasionally it may not attain the resistance to fluctuations of the pH, which is one of the effects of the present invention.

Furthermore, when a salt of (2R)-2-propyloctanoic acid, for example, a sodium salt of (2R)-2-propyloctanoic acid is used, it can be dissolved in water without addition of metal hydroxide.

Nevertheless, the resulting solution has a high pH, and occasionally it may not attain the resistance to pH fluctuations, which is one of the effects of the present invention, as discussed above. Therefore, the medicament of the present invention is preferably a medicament which comprises at least one metal salt of weak acid and optionally further comprises a metal hydroxide.

An appropriate example of the medicament of the present invention is, for example, a medicament which comprises about 1 to about 5 equivalents of a basic metal ion based on 1 equivalent of (2R)-2-propyloctanoic acid or a salt thereof; comprises at least one selected from a metal salt of phosphoric acid, a metal salt of carbonic acid and a metal salt of sulfurous acid, and optionally further comprises a metal hydroxide, as a source of the basic metal ion; and has a pH of about 8.4 to about 9.0, and the like.

Herein, preferred metal salts of phosphoric acid include, for example, trisodium phosphate, disodium hydrogen phosphate, sodium dihydrogen phosphate, or hydrates thereof; preferred metal salts of carbonic acid include, for example, sodium carbonate, sodium hydrogen carbonate, or hydrates thereof; and preferred metal salts of sulfurous acid include, for example, sodium sulfite, sodium hydrogen sulfite, or hydrates thereof. Metal salts of these acids comprising potassium instead of sodium are also preferred.

Furthermore, preferred metal hydroxides include sodium hydroxide, potassium hydroxide and the like. As described above, these metal hydroxides may used in mixtures. The preferred ranges of the contents of the respective metal salt and of the content of the metal hydroxide will be illustrated in the following, as expressed in the weight based on the number of moles of (2R)-2-propyloctanoic acid or a salt thereof. However, these are only exemplary values for the case of using compounds comprising sodium, and if compounds comprising potassium in place of sodium are used, the values should be appropriately modified in accordance with the molecular weight of the element. The contents of the sodium salts of phosphoric acid, carbonic acid or sulfurous acid based on 1 mole of (2R)-2-propyloctanoic acid or a salt thereof, that is, the contents of these salts corresponding to 1 to 5 equivalents are, for example, as follows: (1) about 54.7 g to about 273.2 g of trisodium phosphate; (2) about 71.0 g to about 354.9 g of disodium hydrogen phosphate; (3) about 120.0 g to about 600.0 g of sodium dihydrogen phosphate; (4) about 53.0 g to about 265.0 g of sodium carbonate; (5) about 84.0 g to about 420.0 g of sodium hydrogen carbonate; (6) about 53.0 g to about 265.0 g of sodium sulfite; (7) about 104.0 g to about 520.0 g of sodium hydrogen sulfite; and the like. These contents are all expressed as the weight of a non-solvate (for example, an anhydrate or the like).

In the case of using a solvate (for example, hydrate, etc.) comprising one of these components, it is preferable that the weight of addition, as expressed as the weight deducted of the weight of solvent (for example, water, etc.), fall within the range of the weight of non-solvate as described above.

As to whether it is necessary to add sodium hydroxide and/or potassium hydroxide, it can be determined as described above. In the above-described embodiment, for example, in the case of using disodium hydrogen phosphate, sodium dihydrogen phosphate, sodium hydrogen carbonate, sodium hydrogen sulfite, dipotassium hydrogen phosphate, potassium dihydrogen phosphate, potassium hydrogen carbonate, potassium hydrogen sulfite or the like, it is preferable to add sodium hydroxide and/or potassium hydroxide. However, when sodium hydroxide and/or potassium hydroxide is added, it is preferable to adjust the amount of the added metal salt of weak acid appropriately, preferably so that the total amount of the basic metal ion is 1 to 5 equivalents, while being careful not to impair the buffering ability and not to depart from the preferable range of the pH.

For example, in the case of a medicament comprising (2R)-2-propyloctanoic acid, preferred examples of the medicament comprising sodium hydroxide and/or potassium hydroxide include a medicament comprising about 1 equivalent of the corresponding sodium hydroxide and/or potassium hydroxide and about 1 to about 4 equivalents of the corresponding metal salt of weak acid, for example, disodium hydrogen phosphate, sodium dihydrogen phosphate, sodium hydrogen carbonate, sodium hydrogen sulfite, dipotassium hydrogen phosphate, potassium dihydrogen phosphate, potassium hydrogen carbonate, potassium hydrogen sulfite or the like.

In addition, as a method of using no basic metal ion, it is also possible, by adding at least a certain amount of, for example, tris(hydroxymethyl)aminomethane instead of the above-described metal salts, to provide a medicament having the same effect, that is, to provide a medicament comprising (2R)-2-propyloctanoic acid or a salt thereof in a high concentration, which is resistant to the fluctuation of pH and which can be formulated, without clouding, to an injection having a pH suitable for administration to a patient by using a dissolving liquid and/or a diluting liquid at the time of use. However, if tris(hydroxymethyl)aminomethane is used, it is preferable to use a sterilization method which does not involve heating, such as filtration sterilization, among the sterilization operations as described below for the medicament of the present invention.

The medicament of the present invention may further comprise suitable additives which are generally used for injections. The additives include, for example, aqueous solutions of 70 v/v % N-hydroxyethyl lactamide, D-sorbitol, D-mannitol, DL-methionine, L-aspartic acid, L-alanine, L-arginine, L-glutamic acid, L-lysine, potassium L-gluatamate, sodium L-glutamate, L-cystine, L-cystein, L-histidine, L-methionine, N,N-dimethylacetamide, ascorbic acid, sodium acetyltryptophan, aminoethyl sulfonic acid, aminoacetic acid, gum Arabic, powdered acacia, alpha-thioglycerin, albumin, inositol, ethanol, ethyl urea, ethylenediamine, sodium calcium edetate, sodium edetate, oleic acid, sodium caprylate, sodium carmellose, xylitol, citric acid, sodium citrate, disodium citrate, glycerin, calcium gluconate, sodium gluconate, magnesium gluconate, creatinine, chlorobutanol, gentisic acid ethanolamide, succinic acid, sesame oil, sodium chondroitin sulfate, sodium salicylate, diethanolamine, diethylene triamine pentaacetate, sorbitan sesquioleate, gelatin, gelatin hydrolysate, sorbitan fatty acid ester, soybean oil, thioglycolic acid, sodium thioglycolate, potassium thiocyanate, sodium thiomalate, sodium thiosulfate, camellia oil, dextran 40, dextran 70, sodium desoxycholate, triethanolamine, tromethamol, sodium formaldehyde, sulfoxylate, nicotinic amide, ethyl paraoxybenzoate, butyl paraoxybenzoate, propyl paraoxybenzoate, methyl paraoxybenzoate, hydroxypropyl cellulose, castor oil, potassium pyrosulfite, sodium pyrosulfite, phenol, butyl hydroxyanisole, glucose, propylene glycol, sodium heparinate, benzyl alcohol, polyoxyethylene (160) polyoxypropylene (30) glycol, polyoxyethylene castor oil, polyoxyethylene hydrogenated castor oil, polyoxyethylene hydrogenated castor oil 50, polyoxyethylene hydrogenated castor oil 60, Polysorbate 80, Macrogol 400, Macrogol 4000, maltose, meglumine, sodium methane sulfobenzoate, monoethanolamine, aluminum monostearate, polyoxyethylene sorbitan (20 E.O.) monolaurate, peanut oil, phosphoric acid, dipotassium phosphate, potassium dihydrogen phosphate, sodium sulfite, sodium hydrogen sulfite, benzoic acid, sodium benzoate, benzyl benzoate, aluminum chloride, sodium chloride, benzalkonium chloride, benzethonium chloride, magnesium chloride, zinc chloride, zinc chloride solution, tin(I) chloride, iron(II) chloride, hydrochloric acid, arginine chloride, cystein chloride, lysine chloride, fructose, dried aluminum gel, dried sodium sulfite, dilute hydrochloric acid, highly purified egg yolk lecithin, calcium oxide, zinc oxide, tartaric acid, calcium bromide, sodium bromide, acetic acid, ammonium acetate, sodium acetate, zinc acetate, aluminum hydroxide, purified gelatin, purified soybean lecithin, purified soybean oil, purified sucrose, purified egg yolk lecithin, sodium hydrogen carbonate, water for injection, calcium sugar acid, lactic acid, ethyl lactate, a sodium lactate solution, lactose, urea, concentrated glycerin, glacial acetic acid, anhydrous ethanol, anhydrous citric acid, anhydrous sodium pyrophosphate, anhydrous maleic acid, anhydrous tin(I) chloride, anhydrous sodium acetate, sulfuric acid, potassium aluminum sulfate, potassium sulfate, magnesium sulfate and the like. These additives are generally mixed in the proportions used in conventional injections.

As it is well known to a person skilled in the art, or as it is described in *Iyakuhin Tenkabutsu Jiten* (*Pharmaceutical Additive Dictionary*) (edited by Japan Pharmaceutical Excipients Council) published by Yakuji Nippo Limited in 2000, such additives can be classified according to the intended use, for example, into a stabilizer, a surfactant, a buffer, a pH adjusting agent, a solubilizer, an antioxidant, a defoamer, an isotonic agent, an emulsifier, a suspending agent, a preservative, a soothing agent, a dissolving agent, a solubilizing aid or the like.

Furthermore, these additives may be added in combination of two or more components, if necessary.

The various additives listed herein also include those functioning as the source of the basic metal ion. When additives functioning as the source of the basic metal ion are used, it is also preferable that the total amount of the basic metal ions in the medicament falls preferably within the range of about 1 to about 5 equivalents.

The medicament of the present invention also includes all of those medicaments comprising (2R)-2-propyloctanoic acid or a salt thereof, and a basic metal ion (preferably, about 1 to about 5 equivalents of a basic metal ion based on 1 equivalent of (2R)-2-propyloctanoic acid or a salt thereof).

The content of (2R)-2-propyloctanoic acid or a salt thereof as the active ingredient is not limited, but the amount will be suitable, in the case of a liquid medicament, to be about 2.5 mg to about 100 mg of (2R)-2-propyloctanoic acid or a salt thereof per mL in terms of (2R)-2-propyloctanoic acid. Especially, by taking the method of using the medicament as formulated to an injection by dilution in an infusion or the like into consideration, the content is preferably, for example, about 25 mg to about 100 mg per mL, more preferably about 50 mg to about 100 mg per mL, and particularly preferably about 50 mg per mL. Furthermore, in the case of a solid medicament or a semi-solid medicament, it is suitable to dissolve the medicament in any dissolving liquid (preferably, water (for example, water for injection, etc.), etc.) in a container such as a vial or an ampoule, such that 1 mL of the solution comprises the above-described amount of (2R)-2-propyloctanoic acid or a salt thereof.

When the medicament of the present invention is an aqueous medicament comprising (2R)-2-propyloctanoic acid or a salt thereof in a high concentration (particularly, about 20 mg/mL or more), the medicament takes the form of a micelle water dispersion liquid.

The micelle water dispersion liquid means that micelles, that is, aggregates formed by (2R)-2-propyloctanoic acid or a salt thereof, or aggregates formed from the interaction of (2R)-2-propyloctanoic acid or a salt thereof with a basic metal ion, are homogeneously dispersed in the medium water, and its properties (for example, fluidity or the like) are not significantly different from those of conventional aqueous solutions. By having the form of a micelle water dispersion liquid, the medicament of the present invention can comprises (2R)-2-propyloctanoic acid or a salt thereof in a high concentration while maintaining the operationality equal to that of aqueous solutions. It can be determined on whether or not the medicament is a micelle water dispersion liquid by carrying out conventional methods making use of the properties of micelles, for example, the method of fat staining.

The fat staining method includes, for example, a method of mixing a solution of a fat-soluble dye (for example, Sudan III, piacyanol chloride, Rhodamine 6G, etc.) with the solution under test, followed by centrifugation after a certain period of time, and measuring the absorbance of the supernatant which is inherent to the fat-soluble dye used. If the absorbance of the supernatant can be measured according to this test method, it implies that the fat-soluble dye is present within micelles, that is, micelles have been formed, and thus it is possible to determine that a micelle water dispersion liquid has been formed. It is also possible to define the critical concentration of micelle formation, that is, a critical micelle concentration (CMC), by means of such a test.

The critical micelle concentration cannot be exactly determined since it depends on the substance forming micelles, the type of co-existing ions and the concentration thereof, the ionic strength, and even on temperature. But, in the case of an aqueous medicament comprising about 1 to about 5 equivalents of basic sodium ion based on 1 equivalent of (2R)-2-propyloctanoic acid, the critical micelle concentration is in the range of about 20-25 mg/mL at room temperature.

The medicament of the present invention can be obtained by dissolving (2R)-2-propyloctanoic acid or a salt thereof together with the above-described source of the basic metal ion and, if necessary, with the above-described additives, in water (for example, water for injection, etc.), and filling the solution in a vial or an ampoule, if necessary, followed by lyophilization.

The dissolution process may be carried out in any order. For example, (2R)-2-propyloctanoic acid or a salt thereof may be dissolved in a solution mixed with an aqueous solution of a metal salt of weak acid, which is the source of the basic metal ion (for example, an aqueous solution of trisodium phosphate, disodium hydrogen phosphate, sodium dihydrogen phosphate, sodium carbonate, sodium hydrogen carbonate, sodium sulfite, sodium hydrogen sulfite, tripotassium phosphate, dipotassium hydrogen phosphate, potassium dihydrogen phosphate, potassium carbonate, potassium hydrogen carbonate, potassium sulfite, potassium hydrogen sulfite, or the like), or an aqueous solution of metal hydroxide (for example, an aqueous solution of sodium hydroxide, potassium hydroxide or the like), or the solid of each component may be weighed, mixed, and then dissolved in water.

It is also possible to prepare a clear solution by first adding water to (2R)-2-propyloctanoic acid or a salt thereof to yield a clouded solution, and then adding thereto a necessary amount of a metal salt of weak acid and optionally metal hydroxide. Furthermore, as described above, the metal salt of weak acid in the medicament of the present invention is dissociated in the solution, is brought into equilibrium and exhibits the buffering ability.

The monovalent alkali metal ion which is derived from the metal salt of weak acid or metal hydroxide may react with (2R)-2-propyloctanoic acid to contribute to dissolution thereof by forming a salt. Therefore, the medicament of the present invention may occasionally have the components detected in the solution which are different from the components used in the formulation, that is, the starting materials. For example, a medicament formulated by dissolving (2R)-2-propyloctanoic acid and trisodium phosphate in water, results in the formation of, for example, a sodium salt of (2R)-2-propyloctanoic acid, disodium hydrogen phosphate, sodium dihydrogen phosphate, trisodium phosphate and/or their ions, etc. in the aqueous solution, and in dissolution, leading to equilibrium. Therefore, the medicament of the present invention can be prepared by mixing the solution composition in equilibrium or the components which can constitute the solution composition in equilibrium.

Lyophilization can be carried out by conventional methods. In general, it is preferable to use a method in which the medicament is frozen at a temperature of −25° C. or lower and then dried while elevating the shelf temperature up to 25 to 40° C., and while maintaining the degree of vacuum in the dry chamber at about 13.3 Pa or less.

Furthermore, the medicament, in particular the semi-solid medicament, of the present invention can be obtained by charging, after kneading if necessary, (2R)-2-propyloctanoic acid or a salt thereof, together with the source of the above-described basic metal ion and optionally with the above-described additives, into a vial or an ampoule. Although the semi-solid medicament thus obtained may vary in the state depending on conditions such as the presence or absence of kneading, the temperature, the amount of the added source of the basic metal ion, etc., and for example, when about 1 equivalent of (2R)-2-propyloctanoic acid is mixed with about 3 equivalents of the source of the basic sodium ions and kneaded, the medicament is in the form of a colorless gel agent.

The medicament can be conventionally prepared to an aseptic medicament by subjecting it to the same sterilization procedures as usual injections. Specifically, for example, it is possible to provide an aseptic medicament, after mixing the respective components according to the above-described processes, by subjecting it an operation such as, for example, filtration sterilization with sterilizing filter before charging into suitable containers such as, for example, ampoules or vials, or by subjecting it to an operation such as, for example, irradiation sterilization or high-pressure steam sterilization (autoclaving) after charging into containers.

It is also possible to carry out processes such as filtration by using a dust-free filter (for example, a 0.45 µm methylcellulose membrane, a 0.45 µm Nylon 66 membrane, a 0.45 µm polyfluorovinylidene, etc.), before charging the medicament into their containers, if necessary.

As the sterilization treatment for the medicament of the present invention, high-pressure steam sterilization is preferred. High-pressure steam sterilization is preferably carried out, for example, at 100 to 125° C. for 5 to 30 minutes.

For the "vials", they are preferably made of a glass material or a plastic material such as cyclic polyolefin and polypropylene, which is compatible with the medicament. As preferred vials, vials made of glass materials include, for example, USP TYPE I, II, III or the like, and vials made of plastic materials include, for example, CZ vials (Daikyo Seiko Ltd.) or the like. The shape and size of the vials are not particularly limited.

The capacity of the vials is preferably 100 mL or less, more preferably 40 mL or less, and particularly preferably 20 mL or less. Specific examples of the vials include vials of 30 mm in diameter, vials of 24.5 mm in diameter, vials of 18 mm in diameter, and the like.

For the "ampoules", they are preferably made of a glass material or a plastic material such as polyethylene, polypropylene or the like, which is compatible with the medicament, and ampoules made of a plastic material such as polyethylene, polypropylene or the like are particularly preferred. Preferred ampoules made of glass materials are the above-described USP TYPE I, II, III or the like. The shape and size of the ampoules are not particularly limited. Furthermore, use may be also made of those plastic ampoules having the inner surface glass-coated, or glass ampoules having the inner surface plastic-coated or the like, in which glass materials and plastic materials are combined.

The capacity of the ampoules is preferably 30 mL or less, more preferably 20 mL or less, and particularly preferably 10 mL or less. Specific examples of the ampoules include 20 mL-ampoules, 10 mL-ampoules, 5 mL-ampoules, 3 mL-ampoules, 2 mL-ampoules, 1 mL ampoules and the like, and for example, 20 mL-ampoules, 10 mL-ampoules, 5 mL ampoules or the like are preferred.

The medicament can be provided as pre-filled syringes, in the same manner, by mixing the respective components, and then charging the mixture into a suitable container such as a syringe and subjecting it to the sterilization procedure such as, for example, high-pressure steam sterilization (autoclaving).

For the "syringes" for "pre-filled syringes", they are preferably made of glass material or plastic material such as cyclic polyolefin and polypropylene, which is compatible with the medicament. The syringes made of glass materials are preferably, for example, the above-described USP TYPE I, II, III or the like. The shape and size of the syringes are not particularly limited.

The capacity of the syringes is preferably 30 mL or less, more preferably 20 mL or less, and particularly preferably 10 mL or less. Specific examples of the syringes include 10 mL-syringes, 5 mL-syringes, 3 mL-syringes, 2 mL-syringes, 1 mL-syringes and the like.

In the method for preparation of the medicament of the present invention, when the contents in the container are vigorously foamed so that it requires a long time to obtain a clear solution, it may be attempted to reduce the time taken by using silicone-coated vials, ampoules or syringes.

The silicones used in such coating includes silicone oils (for example, dimethyl polysiloxane, methyl hydrogen polysiloxane, etc.), silicone varnish (for example, methyl silicone varnish, methyl phenyl silicone varnish, etc.) or the like, and a preferred example of silicone is KM-740 (manufactured by Shin-Etsu Chemical Industries).

The medicament of the present invention, in particular the aqueous medicament of pH 7.0 or more, may generate insoluble allotrio when stored in containers made of glass materials. Therefore, when the medicament of the present invention is charged in the above-described vials made of glass materials, ampoules or syringes, generation of insoluble allotrio can be suppressed by coating the inner surfaces (glass surface) of these containers with silicones, or by treating it with silicon dioxide (for example, silicoat treatment, wave plasma chemical vapor deposition treatment, etc.), or by using the containers having their inner surfaces preliminarily treated with silicon dioxide (for example, Silicoat ampoules, silicoat vials, etc. (manufactured by Shiotani Glass, and by Fuji Glass), Type I plus ampoules, Type I Plus vials, etc. (manufactured by SCHOTT)). Thus, it is possible to provide a medicament having no problem on the generation of insoluble allotrio even under long-term storage. The silicone coating may be carried out using the above-described silicones or silicone-based coating agents (for example, dimethyl silicone oil, methylphenyl silicone oil, methyl hydrogen silicone oil, etc.), on the inner surfaces of such containers to a coating thickness of about 100 μm or less, and preferably about 15 to about 50 μm, by conventional methods, for example, thermal evaporation, plasma-enhanced chemical vapor deposition, pulsed-plasma chemical vapor deposition or the like. The treatment with silicon dioxide is carried out by conventional methods, for example, silicoat treatment, wave plasma chemical vapor deposition treatment or the like. Furthermore, when a plastic container is used, there is no problem of generation of insoluble allotrio, and it is possible to provide a medicament which has no problem of generation of insoluble allotrio even under long-term storage, without any treatment.

The medicament of the present invention which is provided as charged in such a vial or an ampoule is administered to the living body, as received in the case of a liquid medicament, or in the case of a solid medicament or a semi-solid medicament, after being dissolved in a dissolving liquid at the time of use, taken out from the vial or the ampoule in a certain desired amount of the entire amount by means of an injection syringe, and then diluted with any diluting liquid (for example, water for injection, saline, a carbohydrate solution, various infusions). Furthermore, the medicament of the present invention which is provided as charged in a pre-filled syringe is also administered to the living body, after a certain desired amount of the entire amount from the pre-filled syringe is diluted with any diluting liquid (for example, water for injection, saline, a carbohydrate solution, various infusions).

As described above, in an embodiment of using the medicament of the present invention, it is preferred to use the medicament of the present invention as diluted in a medium, such as an infusion, which can be intravenously administered. The pH after the dilution is not particularly limited, but when the medicament of the present invention is diluted with an infusion, for example, such that the concentration of the active ingredient (2R)-2-propylocatanoic acid or a salt thereof is about 0.01 to about 20 mg/mL, preferably about 0.1 to about 20 mg/mL, in terms of the amount of (2R)-2-propyloctanoic acid, the pH is about 3.0 to about 10.0, more preferably about 4.0 to about 9.0, and most preferably about 5.0 to about 9.0. In particular, when saline is used as the infusion, after the dilution to the above-described concentration, the pH is about 5.0 to about 9.0, and more preferably about 6.0 to about 9.0.

The infusion used in the dilution of the medicament of the present invention preferably includes, for example, an electrolyte solution, a carbohydrate solution, a vitamin injectable solution, a protein amino acid injectable solution, and the like.

The electrolyte solution as used herein is a solution having electrolytes dissolved in water for injection and include, for example, solutions containing one or at least two of sodium chloride, potassium chloride, calcium chloride, sodium lactate, sodium dihydrogen phosphate, sodium carbonate, magnesium carbonate and the like, lactate Ringer's solution, acetate Ringer's solution, and the like.

A preferred electrolyte solution is, for example, one which is free of divalent metal ions (for example, calcium ions, magnesium ions, etc.) in the infusion. As the electrolyte solution, for example, a solution containing sodium chloride or the like is more preferred, and for example, saline, that is, a solution of 0.9% (w/v) of sodium chloride, is particularly preferred.

The carbohydrate solution is a solution in which saccharides are dissolved in water for injection, and include, for example, solutions containing one or at least two of glucose, fructose, sorbitol, mannitol, dextran and the like. As the carbohydrate solution, for example, a 5 to 70% (w/v) glucose solution are preferred, and for example, a 5% (w/v) glucose solution and a 10% (w/v) glucose solution are in particular preferred.

The protein amino acid injectable solution is a solution in which amino acids are dissolved in water for injection, and include, for example, solutions containing one or at least two of glycine, aspartic acid, lysine and the like. The vitamin injectable solution is a solution in which vitamins are dissolved in water for injection, and include, for example, solutions containing one or at least two of vitamin B1, vitamin C and the like.

A preferred infusion for diluting the medicament of the present invention is, for example, a 0.9% (w/v) sodium chloride solution. Specific examples include commercially available infusions, such as amino acid complex infusions (for example, Aminoleban (manufactured by Otsuka), Amizet B (manufactured by Tanabe), Amizet XB (manufactured by Tanabe), Amiparen (manufactured by Otsuka), Neoamiyu (manufactured by Ajinomoto Pharma), Pleamin-P (manufactured by Fuso), Proteamin 12X (manufactured by Tanabe), Molipron-F (manufactured by Ajinomoto Pharma), etc.), sugar/electrolyte/amino acid solutions for high-calorie infusions (for example, PNTWIN (manufactured by Ajinomoto Pharma), Unicaliq (manufactured by Terumo-Tanabe), etc.), electrolyte infusions (for example, saline, lactate Ringer's solution (for example, Solita (manufactured by Shimizu), Solulact (manufactured by Terumo), Hartmann (manufactured by Koyabashi Seiyaku), Lactec (manufactured by Otsuka), etc.), glucose-reinforced lactate Ringer's solutions (for example, SolulacT D (manufactured by Terumo), Hartmann D (manufactured by Kobayashi Seiyaku), Lactec D (manufactured by Otsuka), etc.), glucose-reinforced acetate Ringer's solutions (for example, Veen-D (manufactured by Nikken Chemical), etc.), sorbitol-reinforced lactate Ringer's solutions (for example Solita S (manufactured by Shimizu), Lactec G (manufactured by Otsuka), etc.), maltose-reinforced lactate Ringer's solutions (for example Solulact TMR (manufactured by Terumo), Potacol R (manufactured by Otsuka), etc.), maltose-reinforced acetate solutions (for example, Actit (manufactured by Nikken Chemical), etc.), EL3 (maintenance fluid for adults; manufactured by Ajinomoto Pharma), 10% EL3 (maintenance fluid; manufactured by Ajinomoto Pharma), EN Supplementary. Fluid (1A, 1B, 2A, 2B, 3A, 3B, 4A, 4B; manufactured by Otsuka), Solita T (Nos. 1, 2, 3, 3-G, 4; manufactured by Shimizu), Physiosol (manufactured by Otsuka), Soldem (1, 2, 3, 4, 5, 6; manufactured by Terumo), etc.), sugar/electrolyte for high-calorie infusions (for example, Triparen (Nos. 1, 2; manufactured by Otsuka), Hicaliq (No. 1, NC-L, No. 2, NC-N, 3, NC-H; manufactured by Terumo), Hicaliq RF (manufactured by Terumo), etc.), sugar/electrolyte/amino acid solutions for high-calorie infusions (for example, PNTWIN (Nos. -1, -2, -3; manufactured by Ajinomoto Pharma), Unicaliq (L, N; manufactured by Terumo-Tanabe), etc.) and the like.

The medicament of the present invention may also be provided in an aseptic form which can be formulated into such medicaments. Such medicaments include, for example, (1) a so-called "kit" preparation in which the components contained in the medicament are supplied in separate containers, (2) a preparation in which the components contained in the medicament are supplied in a different compartment in the same container, and the like. Specific examples such as the above (1) include a preparation, for example, in which (2R)-2-propyloctanoic acid or a salt thereof, and the aqueous solution containing a basic metal ion for dilution of the acid are contained in the separate containers (for example, vials, ampoules, etc.), and specific examples such as the above (2) include a preparation, for example, in which (2R)-2-propyloctanoic acid or a salt thereof, and the aqueous solution containing a basic metal ion for dilution of the acid are contained in separate compartments in the same container (for example, two (or more)-compartmented cylinder ampoules, etc.), and the like. Furthermore, the medicament of the present invention may be supplied together with a diluting agent such as an infusion, in multiple (preferably, two) compartments in the same container. Examples of such a medicament include a preparation contained in a two-compartmented fluid bag, in which the diluting fluid is filled in one compartment and the medicament of the present invention in another compartment.

Application for Medicaments:

The medicament of the present invention which contains (2R)-2-propyloctanoic acid or a salt thereof is useful for the treatment and/or prevention of, for example, neurodegenerative diseases of mammals (for example, human, non-human animals such as monkey, sheep, cow, horse, dog, cat, rabbit, rat, mouse, etc.).

Neurodegenerative diseases include, for example, Alzheimer's disease, Parkinson's disease, amyotrophic lateral sclerosis, progressive supranuclear palsy, olivopontocerebellar atrophy, cerebral stroke (for example, cerebral infarction, cerebral hemorrhage, etc.), or neurofunctional disorders after cerebrospinal trauma (for example, demyelinating diseases (multiple sclerosis, etc.), brain cancer (astrocytoma, etc.), cerebrospinal diseases associated with infection (meningitis, pyocephalus, Creutzfeldt-Jakob disease, AIDS (HIV) dementia, etc.)) and the like. Furthermore, the present medicament is useful as a nerve regeneration promoter, an $S100\beta$ increase inhibitor, or a nerve disorder improver. The medicament of the present invention is administered into the living body under the purpose of treatment and/or prevention of the above-described diseases, after being converted to a form appropriate for administration to a patient by using a dissolving liquid and/or a diluting liquid.

The daily dosage of the injection formulated using the medicament of the present invention depends on the severity of the symptoms; age, sex, or body weight of the patient; the timing or the interval of administration; the type of the active ingredient or the like, and, without being limited, for example, in the case of intravenously administering the medicament as an agent for treating neurodegenerative diseases including cerebral infarction, it is preferable, to set the daily dose of about 2 to about 12 mg per kg of the weight of the patient, when (2R)-2-propyloctanoic acid is used as the active ingredient. More preferably, the dosage is about 2 mg, about 4 mg, about 6 mg, about 8 mg, about 10 mg, about 12 mg or the like per kg of the patient's weight per day. Particularly preferably, the daily dose is about 4 mg, about 6 mg, about 8 mg or about 10 mg per kg of the patient's weight, and the daily dose is in particular suitable at about 4 mg or about 8 mg per kg of the patient's weight. Furthermore, when a salt of (2R)-2-propyloctanoic acid is used as the active ingredient, the daily doses as described above in terms of (2R)-2-propyloctanoic acid, are preferred.

The injections formulated using the medicament of the present invention may be also combined with other medicaments, for example, an anticonvulsant (for example, phenobarbital, mephobarbital, metharbital, primidone, phenyloin, ethotoin, trimethadione, ethosuximide, acetylphenetride, carbamazepine, acetazolamide, diazepam, sodium valproate, etc.), an acetylcholinesterase inhibitor (for example, donepezil hydrochloride, TAK-147, rivastigmine, galantamine, etc.), a neurotrophic factor (for example, ABS-205, etc.), an aldose reductase inhibitor, an antithrombotic (for example, t-PA, heparin, an oral anticoagulant (for example, warfarin, etc.), a synthetic antithrombin drug (for example, gabexate mesylate, nafamostat mesylate, argatroban, etc.), an antiplatelet drug (for example, aspirin, dipyridamole, ticlopidine hydrochloride, beraprost sodium, cilostazol, sodium ozagrel, etc.), a thrombolytic agent (for example, urokinase, tisokinase, alteprase, etc.), a Factor Xa inhibitor, a Factor VIIa inhibitor, a cerebral blood flow and metabolism improver (for example, idebenone, calcium hopantenate, amantadine hydrochloride, meclofenoxate hydrochloride, dihydroergotoxine mesylate, pyrithioxin hydrochloride, γ-aminobutyric acid, bifemelane hydrochloride, lisuride maleate, indeloxazine hydrochloride, nicergoline, propentofylline, etc.), an antioxidant (for example, edaravone, etc.), a glycerin preparation (for example, glyceol, etc.), a β-secretase inhibitor (for example, 6-(4-biphenylyl)methoxy-2-[2-(N,N-dimethylamino)ethyl]tetraline, 6-(4-bi-phenylyl)methoxy-2-(N,N-dimethylamino)methyltetraline, 6-(4-biphenylyl)methoxy-2-(N,N-dipropylamino)methyltetraline, 2-(N,N-dimethylamino)methyl-6-(4'-methoxybiphenyl-4-yl)methoxytetraline, 6-(4-biphenylyl)methoxy-2-[2-(N,N-diethylamino)ethyl]tetraline, 2-[2-(N,N-dimethylamino)ethyl]-6-(4'-methylbiphenyl-4-yl)methoxytetraline, 2-[2-(N,N-dimethylamino)ethyl]-6-(4'-methoxybiphenyl-4-yl)methoxytetraline, 6-(2',4'-dimethoxybiphenyl-4-yl)methoxy-2-[2-(N,N-dimethylamino)ethyl]tetraline, 6-[4-(1,3-benzodioxol-5-yl)phenyl]methoxy-2-[2-(N,N-dimethylamino)ethyl]tetraline, 6-(3',4'-dimethoxybiphenyl-4-yl)methoxy-2-[2-(N,N-dimethylamino)ethyl]tetraline, and optical isomers, salts and hydrates thereof, OM99-2 (WO 01/00663), etc.), a β-amyloid protein aggregation inhibitor (for example, PTI-00703, ALZHEMED (NC-531), PPI-368 (JP-T-11-514333), PPI-558 (JP-T-2001-500852), SKF-74652 (*Biochem. J,* 340 (1), 283-289 (1999)), etc.), a cerebral function activator (for example, aniracetam, nicergoline, etc.), a dopamine receptor agonist (for example, L-dopa, bromocriptine, pergolide, talipexole, pramipexole, cabergoline, amantadine, etc.), a monoamine oxidase (MAO) inhibitor (for example, safrazine, deprenyl, selegiline, ramacemide, riluzole, etc.), a cholinergic blocking agent (for example, trihexyphenidyl, biperiden, etc.), a COMT inhibitor (for example, entacapone, etc.), a therapeutic agent for amyotrophic lateral sclerosis (for example, riluzole, a neurotrophic factor, etc.), a statin-based therapeutic agent for hyperlipidemia (for example, sodium pravastatin, atorvastatin, simvastatin, rosuvastatin, etc.), a fibrate-based therapeutic agent for hyperlipidemia (for example, clofibrate, etc.), an apoptosis inhibitor (for example, CPI-1189, IDN-6556, CEP-1347, etc.), a nerve differentiation and regeneration promoter (for example, leteprinim, xaliproden (SR-57746-A), SB-216763, etc.), a non-steroidal anti-inflammatory drug (for example, meloxicam, tenoxicam, indomethacin, ibuprofen, celecoxib, rofecoxib, aspirin, indomethacin, etc.), a steroid drug (for example, dexamethasone, hexestrol, cortisone acetate, etc.), a sexual hormone or derivatives thereof (for example, progesterone, estradiol, estradiol benzoate, etc.), or the like. Furthermore, it may be also combined with a nicotinic receptor regulator, a γ-secretase inhibitor, a β-amyloid vaccine, a β-amyloid protease, a squalene synthetase inhibiting agent, a therapeutic agent for the abnormal behavior, wandering or the like associated with progress of dementia, a hypotensor, a therapeutic agent for diabetes mellitus, an antidepressant, an antianxiety agent, a disease-modifying antirheumatoid agent, an anticytokine agent (for example, a TNF inhibitor, a MAP kinase inhibitor, etc.), a parathyroid hormone (PTH), a calcium receptor antagonist or the like.

These combination medicaments are only exemplary and are not limited to these.

Other medicaments may be administered in any combination of two or more. Furthermore, the medicaments for combined use include those that have been discovered as well as those that are to be discovered afterward, based on the mechanism described above.

Toxicity:

Toxicity of (2R)-2-propyloctanoic acid or a salt thereof is very low, and it is considered to be sufficiently safe for the use as a pharmaceutical drug. For example, it was found that in a single intravenous administration using a dog, (2R)-2-propyloctanoic acid did not result in death at a dose of 100 mg/kg in any case.

Effect of the Invention:

The present invention provides a medicament comprising (2R)-2-propyloctanoic acid or a salt thereof in a high concentration, which is resistant to pH fluctuations, and which can be formulated without clouding of an injection having a pH suitable for administration to a patient, wherein generation of insoluble allotrio does not occur; and a production process of the same.

BEST MODE FOR CARRYING OUT THE INVENTION

Figure 1:
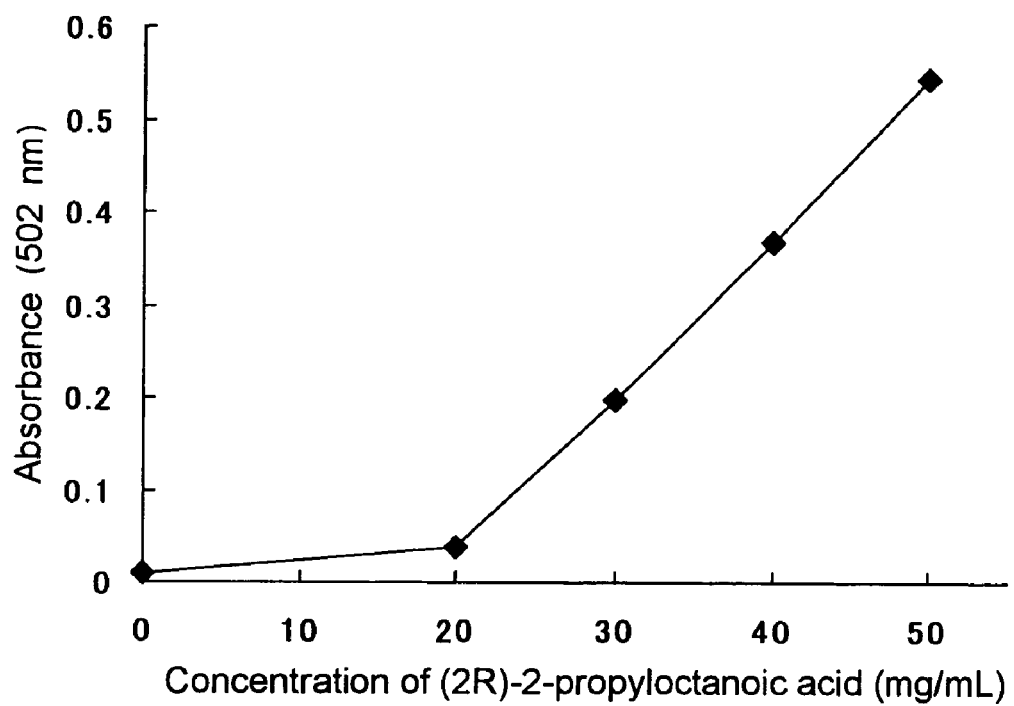
FIG. 1 is a graph showing the results of the confirmation test for micelle formation in the medicament comprising (2R)-2-propyloctanoic acid and a basic metal ions.

Hereinafter, the present invention will be explained by way of Examples, and the present invention is not intended to be limited to these. Furthermore, modifications may be made within the range not departing from the scope of the present invention.

EXAMPLE 1

Preparation of a Medicament Comprising (2R)-2-propyloctanoic acid and trisodium phosphate Trisodium phosphate-dodecahydrate (35.4 g) and (2R)-2-propyloctanoic acid (20.0 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into plastic vials (CZ vials). These vials were capped with rubber stoppers, tightly sealed with aluminum caps, and then autoclaved (123° C., 15 min). Thus, the medicaments were prepared as described in Table 1 below. The dissolved state of each medicament was clear and colorless, and the pH was within the range of 8.4 to 9.0.

TABLE 1

| | Formulation | | | | | |
|---|---|---|---|---|---|---|
| | 1 | 2 | 3 | 4 | 5 | 6 |
| (2R)-2-Propyloctanoic acid (mg) | 50 | 100 | 300 | 400 | 600 | 1200 |
| Trisodium phopshate•dodecahydrate (mg) | 88.5 | 177 | 531 | 708 | 1062 | 2124 |
| Water for injection (in total) (mL) | 1.0 | 2.0 | 6.0 | 8.0 | 12.0 | 24.0 |

EXAMPLE 2

Preparation of a Medicament Comprising (2R)-2-propyloctanoic acid, trisodium phosphate and sodium hydroxide-1

Trisodium phosphate-dodecahydrate (18.0 g), sodium hydroxide (2.1 g) and (2R)-2-propyloctanoic acid (20.0 g) were added to water for injection, and water for injection was further added thereto to give a total volume of 200 mL. The mixture was made to a homogeneous solution and then filtered on a sterilizing filter (Durapore 0.22 μm membrane), and the resulting solution (1 mL, 3 mL, 4 mL, 6 mL, 12 mL and 24 mL) was charged into plastic vials (made of polypropylene). These vials were capped with rubber stoppers, tightly sealed with aluminum caps, and then autoclaved (123° C., 15 min). Thus, the medicaments were prepared as described in Table 2 below. The dissolved state of each medicament was clear and colorless, and the pH was within the range of 8.4 to 9.0.

TABLE 2

| | Formulation | | | | | |
|---|---|---|---|---|---|---|
| | 7 | 8 | 9 | 10 | 11 | 12 |
| (2R)-2-Propyloctanoic acid (mg) | 100 | 300 | 400 | 600 | 1200 | 2400 |
| Trisodium phopshate•dodecahydrate (mg) | 90 | 270 | 360 | 540 | 1080 | 2160 |
| Sodium hydroxide (mg) | 10.7 | 32.1 | 42.8 | 64.2 | 128.4 | 256.8 |
| Water for injection (in total) (mL) | 1.0 | 3.0 | 4.0 | 6.0 | 12.0 | 24.0 |

EXAMPLE 3

Preparation of a Medicament Comprising (2R)-2-propyloctanoic acid, trisodium phosphate and sodium hydroxide-2

Trisodium phosphate-dodecahydrate (4.725 kg), sodium hydroxide (0.5 kg) and (2R)-2-propyloctanoic acid (5.0 kg) were added to water for injection, and water for injection was further added thereto to give a total volume of 100 L. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged with molding (blow fill sealing) into plastic ampoules (made of polypropylene). These ampoules were autoclaved (123° C., 15 min), and thus the medicaments were prepared as described in Table 3 below. The dissolved state of each medicament was clear and colorless, and the pH was within the range of 8.4 to 9.0.

TABLE 3

| | Formulation | | | | | |
|---|---|---|---|---|---|---|
| | 13 | 14 | 15 | 16 | 17 | 18 |
| (2R)-2-Propyloctanoic acid (mg) | 50 | 100 | 300 | 400 | 600 | 1200 |
| Trisodium phopshate•dodecahydrate (mg) | 47.2 | 94.4 | 283 | 378 | 566 | 1133 |
| Sodium hydroxide (mg) | 5.0 | 10.0 | 30.0 | 40.0 | 60.0 | 120.0 |
| Water for injection (in total) (mL) | 1.0 | 2.0 | 6.0 | 8.0 | 12.0 | 24.0 |

EXAMPLE 4

Preparation of a Medicament Comprising (2R)-2-propyloctanoic acid, sodium dihydrogen phosphate and sodium hydroxide-1

Sodium dihydrogen phosphate-dihydrate (3.625 kg), sodium hydroxide (1.95 kg) and (2R)-2-propyloctanoic acid (5.0 kg) were added to water for injection, and water for injection was further added thereto to give a total volume of 100 L. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged with molding (blow fill sealing) into plastic ampoules (made of polypropylene). These ampoules were autoclaved (123° C., 15 min), and thus the medicaments were prepared as described in Table 4 below. The dissolved state of each medicament was clear and colorless, and the pH was within the range of 8.4 to 9.0.

TABLE 4

| | Formulation | | | | | |
|---|---|---|---|---|---|---|
| | 19 | 20 | 21 | 22 | 23 | 24 |
| (2R)-2-Propyloctanoic acid (mg) | 50 | 100 | 300 | 400 | 600 | 1200 |
| Sodium dihydrogen phosphate•dihydrate (mg) | 36.3 | 72.6 | 217.8 | 290.4 | 435.6 | 871.2 |
| Sodium hydroxide (mg) | 19.6 | 39.2 | 117.6 | 156.8 | 235.2 | 470.4 |
| Water for injection (in total) (mL) | 1.0 | 2.0 | 6.0 | 8.0 | 12.0 | 24.0 |

EXAMPLE 5

Preparation of a Medicament Comprising (2R)-2-propyloctanoic acid, sodium dihydrogen phosphate and sodium hydroxide-2

Sodium dihydrogen phosphate-dihydrate (7.3 g), sodium hydroxide (6.0 g) and (2R)-2-propyloctanoic acid (20.0 g)

were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 μL, 12 mL and 24 mL) was charged into syringes made of polypropylene. These syringes were capped and autoclaved (123° C., 15 min), and thus the medicaments were prepared as described in Table 5 below. The dissolved state of each medicament was clear and colorless, and the pH was within the range of 8.4 to 9.0.

TABLE 5

| | Formulation | | | | | |
|---|---|---|---|---|---|---|
| | 25 | 26 | 27 | 28 | 29 | 30 |
| (2R)-2-Propyloctanoic acid (mg) | 50 | 100 | 300 | 400 | 600 | 1200 |
| Sodium dihydrogen phosphate•dihydrate (mg) | 18.2 | 36.4 | 109.2 | 145.6 | 218.4 | 436.8 |
| Sodium hydroxide (mg) | 15.0 | 30.0 | 90.0 | 120.0 | 180.0 | 360.0 |
| Wafer for injection (in total) (mL) | 1.0 | 2.0 | 6.0 | 8.0 | 12.0 | 24.0 |

EXAMPLE 6

Preparation of a Medicament Comprising (2R)-2-propyloctanoic acid, disodium hydrogen phosphate and sodium hydroxide-1

Disodium hydrogen phosphate-dodecahydrate (32.0 g), sodium hydroxide (4.12 g) and (2R)-2-propyloctanoic acid (20.0 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into Silicoat ampoules. These ampoules were sealed and autoclaved (123° C., 15 min), and thus the medicaments were prepared as described in Table 6 below. The dissolved state of each medicament was clear and colorless, and the pH was within the range of 8.4 to 9.0.

TABLE 6

| | Formulation | | | | | |
|---|---|---|---|---|---|---|
| | 31 | 32 | 33 | 34 | 35 | 36 |
| (2R)-2-Propyloctanoic acid (mg) | 50 | 100 | 300 | 400 | 600 | 1200 |
| Disodium hydrogen phosphate•dodecahydrate (mg) | 80 | 160 | 480 | 640 | 960 | 1920 |
| Sodium hydroxide (mg) | 10.3 | 20.6 | 61.8 | 82.4 | 123.6 | 247.2 |
| Water for injection (in total) (mL) | 1.0 | 2.0 | 6.0 | 8.0 | 12.0 | 24.0 |

EXAMPLE 7

Preparation of a Medicament Comprising (2R)-2-propyloctanoic acid, disodium hydrogen phosphate and sodium hydroxide-2

Disodium hydrogen phosphate-dodecahydrate (16.0 g), sodium hydroxide (4.12 g) and (2R)-2-propyloctanoic acid (20.0 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into silicoat vials. These vials were capped with rubber stoppers, tightly sealed with aluminum caps, and then autoclaved (123° C., 15 min). Thus, the medicaments were prepared as described in Table 7 below. The dissolved state of each medicament was clear and colorless, and the pH was within the range of 8.4 to 9.0.

TABLE 7

| | Formulation | | | | | |
|---|---|---|---|---|---|---|
| | 37 | 38 | 39 | 40 | 41 | 42 |
| (2R)-2-Propyloctanoic acid (mg) | 50 | 100 | 300 | 400 | 600 | 1200 |
| Disodium hydrogen phosphate•dodecahydrate (mg) | 40 | 80 | 240 | 320 | 480 | 960 |
| Sodium hydroxide (mg) | 10.3 | 20.6 | 61.8 | 82.4 | 123.6 | 247.2 |
| Water for injection (in total) (mL) | 1.0 | 2.0 | 6.0 | 8.0 | 12.0 | 24.0 |

EXAMPLE 8

Preparation of a Medicament Comprising (2R)-2-propyloctanoic acid and sodium carbonate Sodium carbonate (11.4 g) and (2R)-2-propyloctanoic acid (20.0 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into Type I Plus vials. These vials were capped with rubber stoppers, tightly sealed with aluminum caps, and then autoclaved (123° C., 15 min). Thus, the medicaments were prepared as described in Table 8 below. The dissolved state of each medicament was clear and colorless, and the pH was within the range of 8.4 to 9.0.

TABLE 8

| | Formulation | | | | | |
|---|---|---|---|---|---|---|
| | 43 | 44 | 45 | 46 | 47 | 48 |
| (2R)-2-Propyloctanoic acid (mg) | 50 | 100 | 300 | 400 | 600 | 1200 |
| Sodium carbonate (mg) | 28.5 | 57.0 | 171.0 | 228.0 | 342.0 | 684.0 |
| Water for injection (in total) (mL) | 1.0 | 2.0 | 6.0 | 8.0 | 12.0 | 24.0 |

EXAMPLE 9

Preparation of a Medicament Comprising (2R)-2-propyloctanoic acid, sodium hydrogen carbonate and sodium hydroxide Sodium hydrogen carbonate (9.0 g), sodium hydroxide (3.9 g) and (2R)-2-propyloctanoic acid (20.0 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into syringes made of cyclic polyolefin. These syringes were capped and autoclaved (123° C., 15 min), and thus the medicaments were prepared as described in Table 9 below. The dissolved state of each medicament was clear and colorless, and the pH was within the range of 8.4 to 9.0.

TABLE 9

| | Formulation | | | | | |
|---|---|---|---|---|---|---|
| | 49 | 50 | 51 | 52 | 53 | 54 |
| (2R)-2-Propyloctanoic acid (mg) | 50 | 100 | 300 | 400 | 600 | 1200 |
| Sodium hydrogen carbonate (mg) | 22.5 | 45.0 | 135.0 | 180.0 | 270.0 | 540.0 |
| Sodium hydroxide (mg) | 9.7 | 19.4 | 58.2 | 77.6 | 116.4 | 232.8 |
| Water for injection (in total) (mL) | 1.0 | 2.0 | 6.0 | 8.0 | 12.0 | 24.0 |

EXAMPLE 10

Preparation of a Medicament Comprising (2R)-2-propyloctanoic acid and sodium sulfite Sodium sulfite (24.0 g), sodium hydroxide (3.9 g) and (2R)-2-propyloctanoic acid (20.0 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into plastic vials (CZ vials). These vials were capped with rubber stoppers, tightly sealed with aluminum caps, and then autoclaved (123° C., 15 min). Thus, the medicaments were prepared as described in Table 10 below. The dissolved state of each medicament was clear and colorless, and the pH was within the range of 8.4 to 9.0.

TABLE 10

| | Formulation | | | | | |
|---|---|---|---|---|---|---|
| | 55 | 56 | 57 | 58 | 59 | 60 |
| (2R)-2-Propyloctanoic acid (mg) | 50 | 100 | 300 | 400 | 600 | 1200 |
| Sodium sulfite (mg) | 60 | 120 | 360 | 480 | 720 | 1440 |
| Sodium hydroxide (mg) | 9.7 | 19.4 | 58.2 | 77.6 | 116.4 | 232.8 |
| Water for injection (in total) (mL) | 1.0 | 2.0 | 6.0 | 8.0 | 12.0 | 24.0 |

EXAMPLE 11

Preparation of a Medicament Comprising (2R)-2-propyloctanoic acid, sodium hydrogen sulfite and sodium hydroxide Sodium hydrogen sulfite (20.0 g), sodium hydroxide (4.12 g) and (2R)-2-propyloctanoic acid (20.0 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into Type I plus ampoules. These ampoules were sealed and autoclaved (123° C., 15 min), and thus the medicaments were prepared as described in Table 11 below. The dissolved state of each medicament was clear and colorless, and the pH was within the range of 8.4 to 9.0.

TABLE 11

| | Formulation | | | | | |
|---|---|---|---|---|---|---|
| | 61 | 62 | 63 | 64 | 65 | 66 |
| (2R)-2-Propyloctanoic acid (mg) | 50 | 100 | 300 | 400 | 600 | 1200 |
| Sodium hydrogen sulfite (mg) | 50 | 100 | 300 | 400 | 600 | 1200 |
| Sodium hydroxide (mg) | 10.3 | 20.6 | 61.8 | 82.4 | 123.6 | 247.2 |
| Water for injection (in total) (mL) | 1.0 | 2.0 | 6.0 | 8.0 | 12.0 | 24.0 |

REFERENCE EXAMPLE 1

Preparation of a Medicament Comprising (2R)-2-propyloctanoic acid and tris(hydroxymethyl) aminomethane Tris(hydroxymethyl)aminomethane (26.0 g) and (2R)-2-propyloctanoic acid (20.0 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into Silicoat ampoules. These ampoules were sealed and prepared as described in Table 12 below. The dissolved state of each medicament was clear and color-less, and the pH was within the range of 8.4 to 9.0.

TABLE 12

| | Formulation | | | | | |
|---|---|---|---|---|---|---|
| | 67 | 68 | 69 | 70 | 71 | 72 |
| (2R)-2-Propyloctanoic acid (mg) | 50 | 100 | 300 | 400 | 600 | 1200 |
| Tris(hydroxymethyl)amino-methane (mg) | 80 | 160 | 480 | 640 | 960 | 1920 |
| Water for injection (in total) (mL) | 1.0 | 2.0 | 6.0 | 8.0 | 12.0 | 24.0 |

EXAMPLE 12

Preparation of a Medicament Comprising (2R)-2-propyloctanoic acid-sodium salt and disodium hydrogen phosphate Disodium hydrogen phosphate-dodecahydrate (33.4 g) and (2R)-2-propyloctanoic acid-sodium salt (22.4 g) were added to water for injection, and water for injection was further added thereto to give a total volume of 400 mL. The mixture was made to a homogeneous solution and then filtered on a sterilizing filter (Durapore 0.22 μm membrane), and the resulting solution (1 mL, 2 mL, 6 mL, 8 mL, 12 mL and 24 mL) was charged into plastic vials (made of polypropylene). These vials were capped with rubber stoppers, tightly sealed with aluminum caps, and then autoclaved (123° C., 15 min). Thus, the medicaments were prepared as described in Table 13 below. The dissolved state of each medicament was clear and colorless, and the pH was within the range of 8.4 to 9.0.

TABLE 13

|  | Formulation | | | | | |
| --- | --- | --- | --- | --- | --- | --- |
|  | 73 | 74 | 75 | 76 | 77 | 78 |
| (2R)-2-Propyloctanoic acid•sodium salt (mg) | 55.9 | 111.8 | 335.4 | 447.2 | 670.8 | 1341.6 |
| Disodium hydrogen phosphate•dodecahydrate (mg) | 83.4 | 166.8 | 500.4 | 667.2 | 1000.8 | 2001.6 |
| Water for injection (in total) (mL) | 1.0 | 2.0 | 6.0 | 8.0 | 12.0 | 24.0 |

EXAMPLE 13

Preparation of a Medicament Comprising (2R)-2-propyloctanoic acid, disodium hydrogen phosphate and sodium hydroxide-3

Disodium hydrogen phosphate-dodecahydrate (8.0 kg), sodium hydroxide (1.03 kg) and (2R)-2-propyloctanoic acid (5.0 kg) were added to water for injection, and water for injection was further added thereto to give a total volume of 100 L. The mixture was made to a homogeneous solution and then filtered on a sterilizing filter (Durapore 0.22 μm membrane), and the resulting solution (1 mL, 4 mL, 8 mL, and 20 mL) was charged with molding (blow fill sealing) into plastic ampoules (made of polypropylene). These ampoules were autoclaved (123° C., 15 min), and thus the medicaments were prepared as described in Table 14 below. The dissolved state of each medicament was clear and colorless, and the pH was within the range of 8.4 to 9.0.

TABLE 14

|  | Formulation | | | |
| --- | --- | --- | --- | --- |
|  | 79 | 80 | 81 | 82 |
| (2R)-2-Propyloctanoic acid (mg) | 50 | 200 | 400 | 1000 |
| Disodium hydrogen phosphate•dodecahydrate (mg) | 80 | 320 | 640 | 1600 |
| Sodium hydroxide (mg) | 10.3 | 41.2 | 82.4 | 206.0 |
| Water for injection (in total) (mL) | 1.0 | 4.0 | 8.0 | 20.0 |

EXAMPLE 14

Preparation of a Medicament Comprising (2R)-2-propyloctanoic acid, disodium hydrogen phosphate and sodium hydroxide-4

Disodium hydrogen phosphate dodecahydrate (8.0 kg), sodium hydroxide (1.03 kg) and (2R)-2-propyloctanoic acid (5.0 kg) were added to water for injection, and water for injection was further added thereto to give a total volume of 100 L. The mixture was made to a homogeneous solution and then filtered on a sterilizing filter (Durapore 0.22 μm membrane), and the resulting solution (1 mL, 4 mL, 8 mL, and 20 mL) was charged with molding (blow fill sealing) into plastic ampoules (made of polyethylene). Thus, the medicaments were prepared as described in Table 15 below. The dissolved state of each medicament was clear and colorless, and the pH was within the range of 8.4 to 9.0.

TABLE 15

|  | Formulation | | | |
| --- | --- | --- | --- | --- |
|  | 83 | 84 | 85 | 86 |
| (2R)-2-Propyloctanoic acid (mg) | 50 | 200 | 400 | 1000 |
| Disodium hydrogen phosphate•dodecahydrate (mg) | 80 | 320 | 640 | 1600 |
| Sodium hydroxide (mg) | 10.3 | 41.2 | 82.4 | 206.0 |
| Water for injection (in total) (mL) | 1.0 | 4.0 | 8.0 | 20.0 |

EXAMPLE 15

Preparation of a Medicament Comprising (2R)-2-propyloctanoic acid, disodium hydrogen phosphate and sodium hydroxide-5

Disodium hydrogen phosphate-dodecahydrate (8.0 kg) and (2R)-2-propyloctanoic acid (5.0 kg) were added to water for injection, and an appropriate amount of sodium hydroxide was added thereto to adjust the pH of the mixture to 8.4 to 9.0, and water for injection was further added thereto to give a total volume of 100 L. The mixture was made to a homogeneous solution and then filtered on a sterilizing filter (Durapore 0.22 μm membrane), and the resulting solution (1 mL, 4 mL, 8 mL, and 20 mL) was charged with molding (blow fill sealing) into plastic ampoules (made of polypropylene). These ampoules were autoclaved (123° C., 15 min), and thus the medicaments were prepared as described in Table 16 below. The dissolved state of each medicament was clear and colorless.

TABLE 16

|  | Formulation | | | |
| --- | --- | --- | --- | --- |
|  | 87 | 88 | 89 | 90 |
| (2R)-2-Propyloctanoic acid (mg) | 50 | 200 | 400 | 1000 |
| Disodium hydrogen phosphate•dodecahydrate (mg) | 80 | 320 | 640 | 1600 |
| Sodium hydroxide (for adjustment of pH to 8.4 to 9.0) | suitable amount | suitable amount | suitable amount | suitable amount |
| Water for injection (in total) (mL) | 1.0 | 4.0 | 8.0 | 20.0 |

EXAMPLE 16

Preparation of a Medicament Comprising (2R)-2-propyloctanoic acid, disodium hydrogen phosphate and sodium hydroxide-6

Disodium hydrogen phosphate-dodecahydrate (8.0 kg) and (2R)-2-propyloctanoic acid (5.0 kg) were added to water for injection, and an appropriate amount of sodium hydroxide was added thereto to adjust the pH of the mixture to 8.4 to 9.0, and water for injection was further added thereto to give a total volume of 100 L. The mixture was made to a homogeneous solution and then filtered on a sterilizing filter (Durapore 0.22 μm membrane), and the resulting solution (1 mL, 4 mL, 8 mL, and 20 mL) was charged with molding (blow fill sealing) into plastic ampoules (made of polyethylene). Thus, the medicaments were prepared as described in Table 7 below. The dissolved state of each medicament was clear and colorless.

TABLE 17

|  | Formulation | | | |
| --- | --- | --- | --- | --- |
|  | 91 | 92 | 93 | 94 |
| (2R)-2-Propyloctanoic acid (mg) | 50 | 200 | 400 | 1000 |
| Disodium hydrogen phosphate•dodecahydrate (mg) | 80 | 320 | 640 | 1600 |
| Sodium hydroxide (for adjustment of pH to 8.4 to 9.0) | suitable amount | suitable amount | suitable amount | suitable amount |
| Water for injection (in total) (mL) | 1.0 | 4.0 | 8.0 | 20.0 |

EXAMPLE 17

Preparation of a Medicament Comprising (2R)-2-propyloctanoic acid, disodium hydrogen phosphate and sodium hydroxide-7

Disodium hydrogen phosphate-dodecahydrate (8.0 kg) and (2R)-2-propyloctanoic acid (5.0 kg) were added to water for injection, and an appropriate amount of sodium hydroxide was added thereto to adjust the pH of the mixture to 8.4 to 9.0, and water for injection was further added thereto to give a total volume of 100 L. The mixture was made to a homogeneous solution and then filtered on a sterilizing filter (Durapore 0.22 μm membrane), and the resulting solution (1 mL, 4 mL, 8 mL, and 20 mL) was charged with molding (blow fill sealing) into plastic syringes (made of cyclic polyolefin). These syringes were autoclaved (123° C., 20 min), and thus the medicaments were prepared as described in Table 18 below. The dissolved state of each medicament was clear and colorless.

TABLE 18

|  | Formulation | | | |
| --- | --- | --- | --- | --- |
|  | 95 | 96 | 97 | 98 |
| (2R)-2-Propyloctanoic acid (mg) | 50 | 200 | 400 | 1000 |
| Disodium hydrogen phosphate•dodecahydrate (mg) | 80 | 320 | 640 | 1600 |

TABLE 18-continued

|  | Formulation | | | |
| --- | --- | --- | --- | --- |
|  | 95 | 96 | 97 | 98 |
| Sodium hydroxide (for adjustment of pH to 8.4 to 9.0) | suitable amount | suitable amount | suitable amount | suitable amount |
| Water for injection (in total) (mL) | 1.0 | 4.0 | 8.0 | 20.0 |

EXAMPLE 18

Preparation of a Medicament Comprising (2R)-2-propyloctanoic acid, disodium hydrogen phosphate and sodium hydroxide-8

Disodium hydrogen phosphate-dodecahydrate (8.0 kg), sodium hydroxide (1.06 kg) and (2R)-2-propyloctanoic acid (5.0 kg) were added to water for injection, and water for injection was further added thereto to give a total volume of 100 L. The mixture was made to a homogeneous solution and then filtered on a sterilizing filter (Durapore 0.22 μm membrane), and the resulting solution (1 mL, 4 mL, 8 mL, and 20 mL) was charged with molding (blow fill sealing) into plastic ampoules (made of polyethylene). Thus, the medicaments were prepared as described in Table 19 below. The dissolved state of each medicament was clear and colorless, and the pH was within the range of 8.4 to 9.0.

TABLE 19

|  | Formulation | | | |
| --- | --- | --- | --- | --- |
|  | 99 | 101 | 102 | 103 |
| (2R)-2-Propyloctanoic acid (mg) | 50 | 200 | 400 | 1000 |
| Disodium hydrogen phosphate•dodecahydrate (mg) | 80 | 320 | 640 | 1600 |
| Sodium hydroxide (mg) | 10.6 | 42.4 | 84.8 | 212 |
| Water for injection (in total) (mL) | 1.0 | 4.0 | 8.0 | 20.0 |

EXAMPLE 19

Preparation of a Medicament Comprising (2R)-2-propyloctanoic acid, disodium hydrogen phosphate and sodium hydroxide-9

Disodium hydrogen phosphate-dodecahydrate (8.0 kg), sodium hydroxide (1.06 kg) and (2R)-2-propyloctanoic acid (5.0 kg) were added to water for injection, and water for injection was further added thereto to give a total volume of 100 L. The mixture was made to a homogeneous solution and then filtered on a sterilizing filter (Durapore 0.22 μm membrane), and the resulting solution (1 mL, 4 mL, 8 mL, and 20 mL) was charged with molding (blow fill sealing) into plastic ampoules (made of polypropylene). These ampoules were autoclaved (123° C., 15 min), and thus the medicaments were prepared as described in Table 20 below. The dissolved state of each medicament was clear and colorless, and the pH was within the range of 8.4 to 9.0.

TABLE 20

| | Formulation | | | |
|---|---|---|---|---|
| | 104 | 105 | 106 | 107 |
| (2R)-2-Propyloctanoic acid (mg) | 50 | 200 | 400 | 1000 |
| Disodium hydrogen phosphate•dodecahydrate (mg) | 80 | 320 | 640 | 1600 |
| Sodium hydroxide (mg) | 10.6 | 42.4 | 84.8 | 212 |
| Water for injection (in total) (mL) | 1.0 | 4.0 | 8.0 | 20.0 |

EXAMPLE 20

Preparation of a Medicament Comprising (2R)-2-propyloctanoic acid, disodium hydrogen phosphate and sodium hydroxide-10

Disodium hydrogen phosphate-dodecahydrate (8.0 kg), sodium hydroxide (1.06 kg) and (2R)-2-propyloctanoic acid (5.0 kg) were added to water for injection, and water for injection was further added thereto to give a total volume of 100 L. The mixture was made to a homogeneous solution and then filtered on a sterilizing filter (Durapore 0.22 μm membrane), and the resulting solution (1 mL, 4 mL, 8 mL, and 20 mL) was charged with molding (blow fill sealing) into plastic syringes (made of cyclic polyolefin). These syringes were autoclaved (123° C., 20 min), and thus the medicaments were prepared as described in Table 21 below. The dissolved state of each medicament clear and colorless, and the pH was within the range of 8.4 to 9.0.

TABLE 21

| | Formulation | | | |
|---|---|---|---|---|
| | 108 | 109 | 110 | 111 |
| (2R)-2-Propyloctanoic acid (mg) | 50 | 200 | 400 | 1000 |
| Disodium hydrogen phosphate•dodecahydrate (mg) | 80 | 320 | 640 | 1600 |
| Sodium hydroxide (mg) | 10.6 | 42.4 | 84.8 | 212 |
| Water for injection (in total) (mL) | 1.0 | 4.0 | 8.0 | 20.0 |

EXAMPLE 21

Confirmation Test of Micelle Formation (1) Preparation of (2R)-2-propyloctanoic acid solution (2R)-2-Propyloctanoic acid (5.0 g) and trisodium phosphate-dodecahydrate (9.18 g) were added to water for injection, and water for injection was further added thereto to give a total volume of 100 mL. The mixture was made into a homogeneous solution and then diluted with water for injection to prepare aqueous solutions having concentrations of (2R)-2-propyloctanoic acid of 20 mg/mL, 30 mg/mL, 40 mg/mL and 50 mg/mL, respectively.

(2) Preparation of Sudan III Solution

A fat-soluble dye Sudan III (about 100 mg) was added to ethanol (50 mL), and the mixture was subjected to ultrasonification and then to filtration on a 0.45 μm membrane. Thus, a Sudan III solution was prepared.

(3) Confirmation of Micelle Formation

Into a spitz made of glass, the Sudan III solution prepared in the above (2) (400 μL) was added, and ethanol was evaporated Each of the (2R)-2-propyloctanoic acid solutions of various concentrations prepared in the above (1) was added thereto, and the mixture was subjected to sonication and stirring. Then, the resulting mixture was left at room temperature for 1 day and then centrifuged (3000 rpm, 15 min). The absorbance of the supernatant was measured at a wavelength of 502 nm.

As a result, it was found that the absorbance increased with the concentration at a concentration of 20 mg/mL or above, and micelle formation occurred in the vicinity of about 20 mg/mL. One example is shown in FIG. 1.

EXAMPLE 22

Preparation of (2R)-2-propyloctanoic acid-sodium salt

To an ethanol (24.3 mL) solution of (2R)-2-propyloctanoic acid (4.647 g), an aqueous solution of 1 N sodium hydroxide (24.3 mL) was added at 0° C. The reaction mixture was stirred at room temperature for 2 hours and concentrated to give a (2R)-2-propyloctanoic acid-sodium salt (4.93 g) having the following properties:

TLC: Rf 0.34 (n-hexane:ethyl acetate=4:1);
NMR (CD$_3$OD): δ 2.26-2.08 (1H, m), 1.63-1.12 (14H, m), 0.95-0.82 (6H, m);
IR(KBr): 3431, 2959, 2930, 2858, 1553, 1459, 1415, 1378, 1114, 725 cm$^{-1}$.

Figure 2:
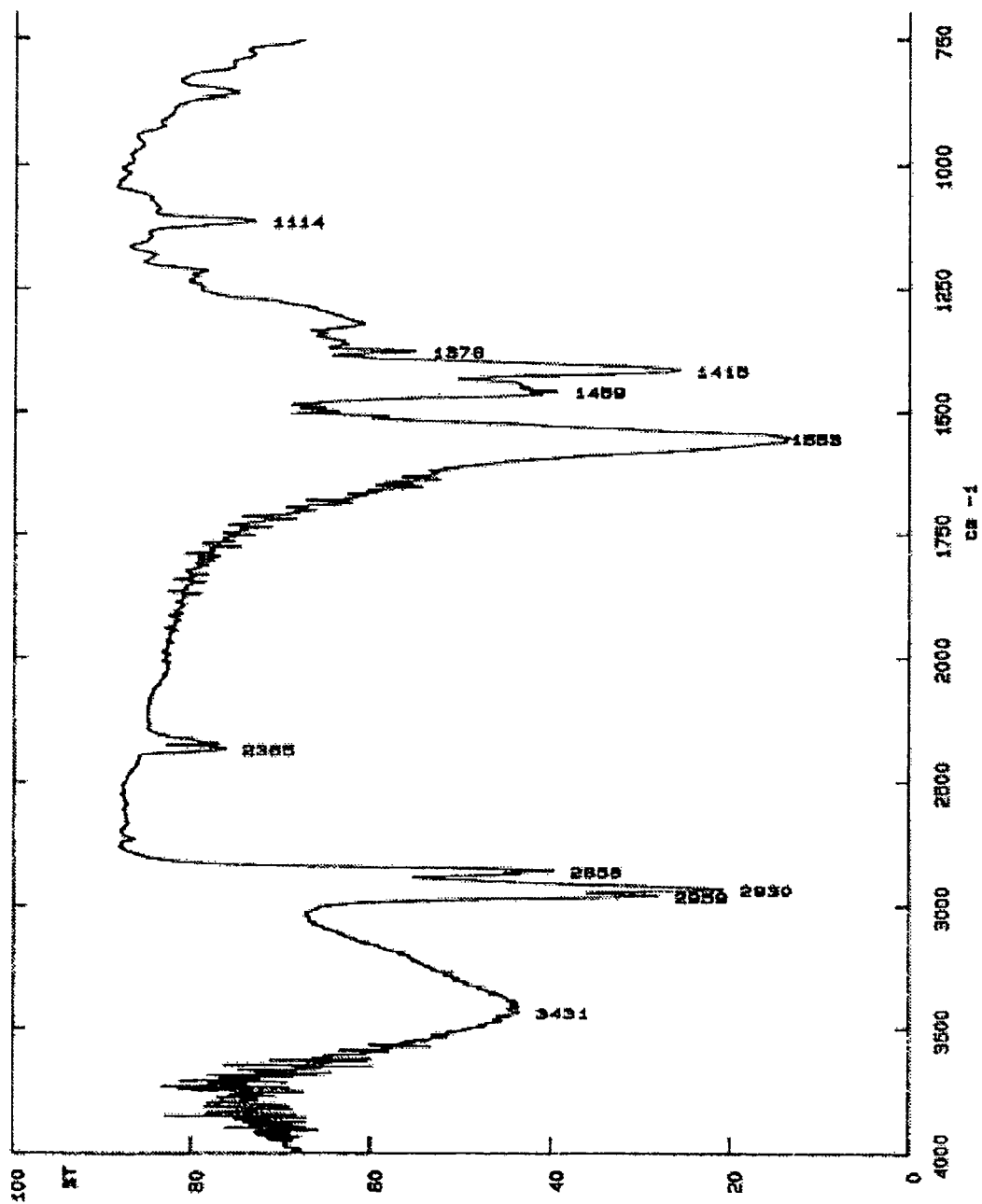
FIG. 2 is an IR absorbance spectrum chart for sodium salt of (2R)-2-propyloctanoic acid.

The IR absorption spectrum chart obtained from measurement of the product is presented in FIG. 2.

Figure 3:
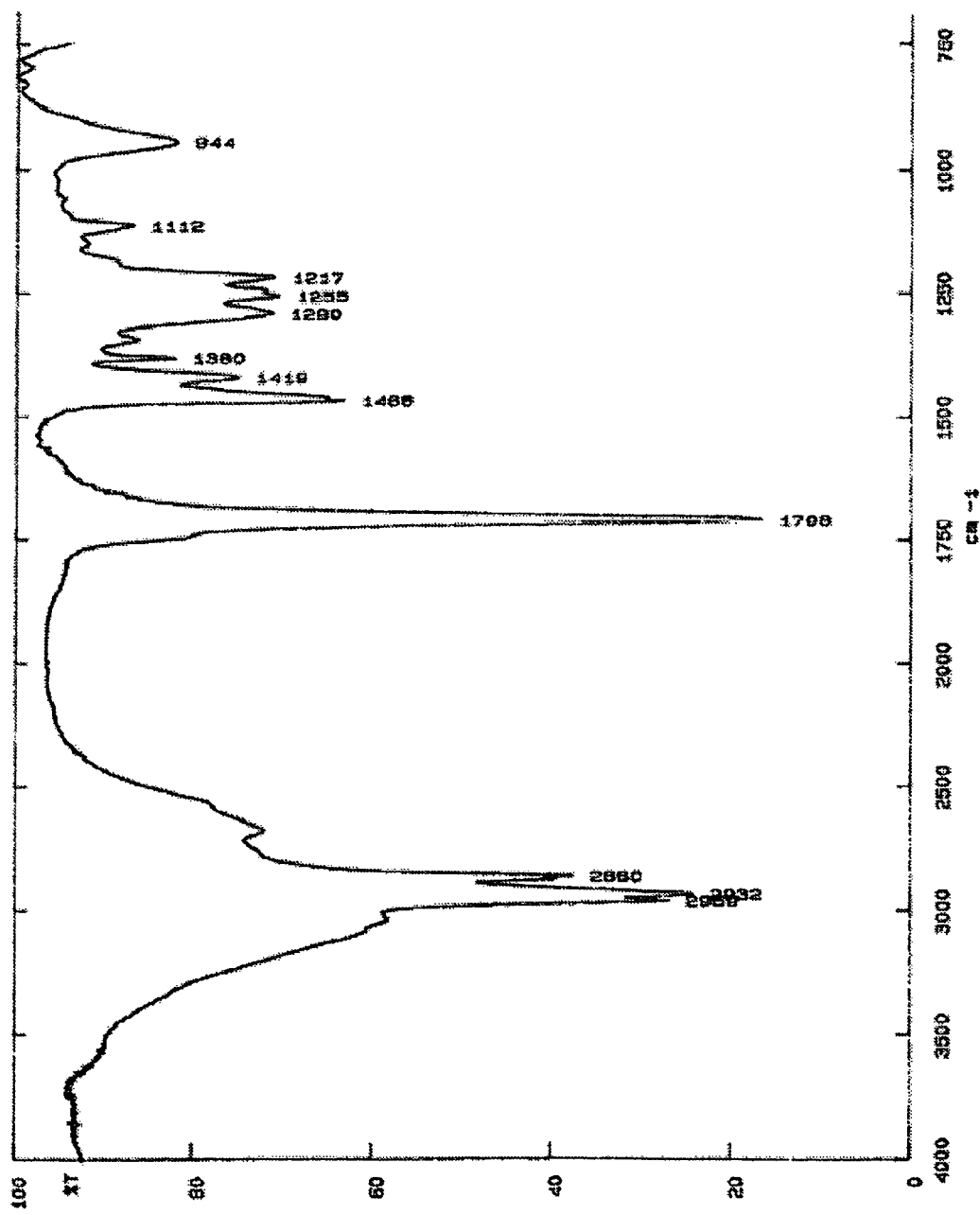
FIG. 3 is an IR absorbance spectrum chart for (2R)-2-propyloctanoic acid.

In addition, the IR absorption spectrum data for (2R)-2-propyloctanoic acid used as the starting material were as follows. A chart thereof is presented in FIG. 3.

IR (neat): 2959, 2932, 2860, 1708, 1466, 1419, 1380, 1290, 1255, 1217, 1112, 944 cm$^{-1}$.

INDUSTRIAL APPLICABILITY

The medicament of the present invention is a medicament comprising (2R)-2-propyloctanoic acid in a high concentration, which can be formulated to an injection of (2R)-2-propyloctanoic acid by using a dissolving liquid and/or a diluting liquid at the time of use. The medicament of the present invention is an excellent injection precursor, which: (1) is resistant to the fluctuation of pH, (2) is not clouded upon formulation of an injection, and (3) does not generate insoluble allotrio. It is also applicable as a medicament.

The invention claimed is:

1. A liquid medicament for preparing injection, comprising a micelle water dispersion liquid of
    (a) (2R)-2-propyloctanoic acid or a salt thereof and
    (b) about 1 to about 5 equivalents of a basic metal ion based on 1 equivalent of (2R)-2-propyloctanoic acid or a salt thereof,
    wherein the basic metal ion is supplied by at least one selected from a metal salt of phosphoric acid, and optionally a metal hydroxide;
    and wherein the mediacament has a pH of about 8.4 to about 9.0.

2. The medicament according to claim 1, wherein the basic metal ion is supplied by at least one selected from trisodium phosphate, disodium hydrogen phosphate, and sodium dihydrogen phosphate, and optionally sodium hydroxide.

3. The medicament according to claim 2, wherein the source of the basic metal ion is (1) trisodium phosphate, (2) disodium hydrogen phosphate and sodium hydroxide, or (3) sodium dihydrogen phosphate and sodium hydroxide.

4. The medicament according to claim 1, wherein the salt of (2R)-2-propyloctanoic acid is a sodium salt.

5. The medicament according to claim 1, which comprises about 25 to about 100 mg of (2R)-2-propyloctanoic acid or a salt thereof per mL.

6. The medicament according to claim 1, which is filled in a plastic container, a glass container of which inner surface is coated with silicone, or a glass container of which inner surface is surface-treated with silicon dioxide.

7. The medicament according to claim 1, which has improved solubility in an infusion.

8. A process for producing a medicament comprising (2R)-2-propyloctanoic acid or a salt thereof and a basic metal ion according to claim 1, which comprises dissolving (2R)-2-propyloctanoic acid or a salt thereof, one or at least two selected from a metal salt of phosphoric acid, a metal salt of carbonic acid and a metal salt of sulfurous acid, and optionally metal hydroxide in water to thereby prepare a solution comprising about 2.5 to about 100 mg/mL of (2R)-2-propyloctanoic acid or a salt thereof and having a pH of about 8.4 to about 9.0; and filling the solution into a plastic container or a glass container of which inner surface is surface-treated with silicon dioxide, followed by high pressure steam sterilization.

9. A method for using a basic metal ion to prepare a medicament according to claim 1, which comprises preparing about 1 to about 5 equivalents of the source of the basic metal ion based on 1 equivalent of (2R)-2-propyloctanoic acid and water as a solvent; and mixing (2R)-2-propyloctanoic acid with water in the presence of the basic metal ion to thereby dissolve (2R)-2-propyloctanoic acid in water.

10. The medicament according to claim 3, wherein the source of the basic metal ion is disodium hydrogen phosphate and sodium hydroxide.

11. The medicament according to claim 10, which comprises, per mL, about 50 mg of (2R)-2-propyloctanoic acid, about 80 mg of disodium hydrogen phosphate-dodecahydrate and sodium hydroxide.

12. A container made of plastics, which is filled with 4 mL, 8 mL or 20mL of the medicament according to claim 11.

13. The container according to claim 12, which is an ampoule made of polyethylene or polypropylene, or a syringe made of cyclic polyolefin.

14. A liquid medicament comprising a micelle water dispersion liquid of about 25 mg to about 100 mg of (2R)-2-propyloctanoic acid per mL and about 1 to about 5 equivalents of a basic sodium ion based on 1 equivalent of (2R)-2-propyloctanoic acid, wherein the basic metal ion is supplied by disodium hydrogen phosphate and sodium hydroxide; and wherein the medicament has a pH of about 8.4 to about 9.0.

15. The medicament according to claim 14, which is filled in an ampoule made of polyethylene or polypropylene, or in a syringe made of cyclic polyolefin.

16. A liquid medicament for preparing injection, comprising a micelle water dispersion liquid of
   (a) about 25 to about 100 mg of (2R)-2-propyloctanoic acid per mL and
   (b) about 1 to about 5 equivalents of a basic sodium ion based on 1 equivalent of (2R)-2-propyloctanoic acid,
   wherein the basic metal ion is supplied by disodium hydrogen phosphate and sodium hydroxide; and wherein the medicament has a pH of about 8.4 to about 9.0.

17. A liquid medicament for preparing injection for preparing an aqueous injectable solution without clouding, comprising a micelle water dispersion liquid of
   (a) about 25 to about 100 mg of (2R)-2-propyloctanoic acid per mL and
   (b) about 1 to about 5 equivalents of a basic sodium ion based on 1 equivalent of (2R)-2-propyloctanoic acid,
       wherein the basic metal ion is supplied by disodium hydrogen phosphate and sodium hydroxide; and wherein the mediacament has a pH of about 8.4 to about 9.0.

* * * * *